US009328163B2

(12) United States Patent
Barbeito et al.

(10) Patent No.: US 9,328,163 B2
(45) Date of Patent: May 3, 2016

(54) POST-TRANSLATIONALLY MODIFIED NEUROTROPHIN ANTIBODIES

(71) Applicants: INSTITUT PASTEUR, Paris (FR); INSTITUTO DE INVESTIGACIONES BIOLOGICAS CLEMENTE ESTABLE, Montevideo (UY); FACULTAD DE MEDICINA, UNIVERSIDAD DE LA REPUBLICA, Montevideo (UY); CENTRE NATIONAL DE LA RECHERCHE SCIENTIFIQUE, Paris (FR)

(72) Inventors: Luis Barbeito, Montevideo (UY); Mariana Pehar, Middleton, WI (US); Patricia Cassina, Montevideo (UY); Pedro M. Alzari, Paris (FR)

(73) Assignees: INSTITUT PASTEUR, Paris (FR); INSTITUTO DE INVESTIGACIONES BIOLOGICAS CLEMENTE ESTABLE, Montevideo (UY); FACULTAD DE MEDICINA, UNIVERSIDAD DE LA REPUBLICA, Montevideo (UY); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 70 days.

(21) Appl. No.: 14/037,973

(22) Filed: Sep. 26, 2013

(65) Prior Publication Data

US 2014/0178384 A1 Jun. 26, 2014

Related U.S. Application Data

(63) Continuation of application No. 12/374,485, filed as application No. PCT/EP2007/006528 on Jul. 23, 2007, now abandoned.

(30) Foreign Application Priority Data

Jul. 24, 2006 (EP) ..................................... 06291195

(51) Int. Cl.
*C07K 16/22* (2006.01)
*A61K 39/395* (2006.01)
*C07K 14/475* (2006.01)
*C07K 14/48* (2006.01)
*A61K 38/00* (2006.01)

(52) U.S. Cl.
CPC ............. *C07K 16/22* (2013.01); *A61K 39/3955* (2013.01); *C07K 14/475* (2013.01); *C07K 14/48* (2013.01); *A61K 38/00* (2013.01)

(58) Field of Classification Search
None
See application file for complete search history.

(56) References Cited

U.S. PATENT DOCUMENTS

2006/0275290 A1 12/2006 Barbeito et al.

FOREIGN PATENT DOCUMENTS

WO WO 2005/014039 2/2005

OTHER PUBLICATIONS

Frazi Er, W. A. et al., "Topography of Mouse 2.5S Nerve Growth Factor. Reactivity of Tyrosine and Tryptophan", Biochemistry, vol. 12, No. 17, pp. 3281-3293 (1973) XP-002403669.
Peluffo, H. et al., "Induction of Motor Neuron Apoptosis by Free 3-Nitro-Tyrosine", Journal of Neurochemistry, vol. 89, No. 3, pp. 602-612 (2004) XP-002403670.
Pehar, M. et al., "Astrocytic Production of Nerve Growth Factor in Motor Neuron Apoptosis: Implications for Amyotrophic AV Lateral Sclerosis", Journal of Neurochemistry, vol. 89, pp. 464-473 (2004) XP-002286440.
Ischiropoulos, H., "Biological Selectivity and Functional Aspects of Protein Tyrosine Nitration", Biochemical and Biophysical Research Communication, vol. 305, No. 3, 6, pp. 776-783 (2003) XP-002403671.
Levi-Montalcini, R. et al., "Nerve Growth Factor", Physiological Reviews, vol. 48, No. 3, pp. 534-569, (1968) XP-008070199.
Hefti, F.F. et al.,"Novel Class of Pain Drugs Based on Antagonism of NGF", Trends in Pharmacological Sciences, vol. 27, No. 2, pp. 85-91 (2006) XP-005278494.
Pehar, M. et al., "Peroxynitrite Transforms Nerve Growth Factor Into an Apoptotic Factor for Motor Neurons", Free Radical Biology & Imedicine, vol. 41, No. 11, pp. 1632-1644 (2006) XP-005719645.

*Primary Examiner* — Robert C Hayes
(74) *Attorney, Agent, or Firm* — Law Office of Salvatore Arrigo and Scott Lee, LLP

(57) ABSTRACT

The present invention describes that neurotrophins undergo post-translational modifications, and that these post-translational modifications mediate the pro-apoptotic and/or pro-neurite activity of neurotrophins. These post-translational modifications notably include nitration and the formation of conformationally-different dimers, as well as of abnormal oligomers, such as tetramers and octamers. The invention further relates to compounds that compete with such modified neurotrophins, as well as to compounds that bind to these modified neurotrophins. The invention thus provides useful agents for the treatment of the conditions or diseases involving chronic pain and/or neuron loss.

12 Claims, 15 Drawing Sheets

```
LOCUS       AAA39818                307 aa            linear   ROD 27-APR-1993
DEFINITION  nerve growth factor.
ACCESSION   AAA39818
VERSION     AAA39818.1  GI:387494
DBSOURCE    locus MUSNGF accession M35075.1
KEYWORDS
SOURCE      Mus musculus (house mouse)
  ORGANISM  Mus musculus
            Eukaryota; Metazoa; Chordata; Craniata; Vertebrata;
Euteleostomi;
            Mammalia; Eutheria; Euarchontoglires; Glires; Rodentia;
            Sciurognathi; Muroidea; Muridae; Murinae; Mus.
REFERENCE   1  (residues 1 to 307)
  AUTHORS   Scott,J., Selby,M., Urdea,M., Quiroga,M., Bell,G.I. and
Rutter,W.J.
  TITLE     Isolation and nucleotide sequence of a cDNA encoding the
precursor
            of mouse nerve growth factor
  JOURNAL   Nature 302 (5908), 538-540 (1983)
   PUBMED   6336309
FEATURES             Location/Qualifiers
     source          1..307
                     /organism="Mus musculus"
                     /db_xref="taxon:10090"
                     /tissue_type="submaxillary gland"
                     /dev_stage="male"
     Protein         1..307
                     /product="nerve growth factor"
     sig_peptide     1..187
                     /gene="NGF"
     mat_peptide     188..305
                     /gene="NGF"
                     /product="nerve growth factor"
     Region          195..>298
                     /region_name="Nerve growth factor (NGF or beta-NGF)"
                     /note="NGF"
                     /db_xref="CDD:47479"
     CDS             1..307
                     /gene="NGF"
                     /coded_by="M35075.1:96..1019"
ORIGIN
        1 mlclkpvklg slevghgqhg gvlacgravq gagwhagpkl tsvsgpnkgf akdaafytgr
       61 sevhsvmsml fytlitafli gvqaepytds nvpegdsvpe ahwtklqhsl dtalrrarsa
      121 ptapiaarvt gqtrnitvdp rlfkkrrlhs prvlfstqpp ptssdtldld fqahgtipfn
      181 rthrskrsst hpvfhmgefs vcdsvsvwvg dkttatdikg kevtvlaevn innsvfrqyf
      241 fetkcrasnp vesgcrgids khwnsyctt  htfvkalttd ekqaawrfir idtacvcvls
      301 rkatrrg
//
``` mouse NGF = SEQ ID NO: 3

FIGURE 11A

```
NP_002497. nerve growth fact...[gi:70995319]
LOCUS           NP_002497                241 aa            linear    PRI 07-MAY-2006
DEFINITION      nerve growth factor, beta polypeptide precursor [Homo sapiens].
ACCESSION       NP_002497
VERSION         NP_002497.2  GI:70995319
DBSOURCE        REFSEQ: accession NM_002506.2
SOURCE          Homo sapiens (human)
  ORGANISM      Homo sapiens
                Eukaryota; Metazoa; Chordata; Craniata; Vertebrata;
                Euteleostomi; Mammalia; Eutheria; Euarchontoglires; Primates;
                Haplorrhini; Catarrhini; Hominidae; Homo.
                Summary: This gene is a member of the NGF-beta family and
                encodes a secreted protein which homodimerizes and is incorporated
                into a larger complex. This protein has nerve growth stimulating
                activity and the complex is involved in the regulation of growth and
                the differentiation of sympathetic and certain sensory neurons.
                Mutations in this gene have been associated with hereditary sensory
                and autonomic neuropathy, type 5 (HSAN5), and dysregulation of this
                gene's expression is associated with allergic rhinitis.
FEATURES                 Location/Qualifiers
     source              1..241
                         /organism="Homo sapiens"
                         /db_xref="taxon:9606"
                         /chromosome="1"
                         /map="1p13.1"
     Protein             1..241
                         /product="nerve growth factor, beta polypeptide precursor"
                         /note="nerve growth factor, beta subunit; beta-nerve
                         growth factor"
     sig peptide         1..18
                         /calculated_mol_wt=2034
     mat peptide         19..241
                         /product="nerve growth factor, beta polypeptide"
                         /calculated_mol_wt=24943
     Region              129..>232
                         /region_name="Nerve growth factor (NGF or beta-NGF)"
                         /note="NGF"
                         /db_xref="CDD:47479"
     CDS                 1..241
                         /gene="NGFB"
                         /coded_by="NM_002506.2:170..895"
                         /go_function="growth factor activity; signal
transducer
                         activity [pmid 6688123]"
                         /go_process="cell-cell signaling; development"
                         /db_xref="CCDS:CCDS882.1"
                         /db_xref="GeneID:4803"
                         /db_xref="HGNC:7808"
                         /db_xref="HPRD:08874"
                         /db_xref="MIM:162030"
ORIGIN
        1 msmlfytlit afligiqaep hsesnvpagh tipqahwtkl qhsldtalrr arsapaaaia
       61 arvagqtrni tvdprlfkkr rlrsprvlfs tqppreaadt qdldfevgga apfnrthrsk
      121 rsshpifhr gefsvcdsvs vwvgdkttat dikgkevmvl gevninnsvf kqyffetkcr
      181 dpnpvdsgcr gidskhwnsy cttthtfvka ltmdgkqaaw rfiridtacv cvlsrkavrr
      241 a
//                                                          human NGF = SEQ ID NO: 4
```

FIGURE 11B

```
1      sst hpvfhmgefs vcdsvsvwg dkttatdikg kevtvlaevn
44     innsvfrqyf fetkcrasnp vesgcrgids khwnsycttt
84     htfvkalttd ekqaawrfir idtacvcvls rkatr
```

= mature mouse NGF (= aa188-305 from SEQ ID NO: 3) = SEQ ID NO: 1

FIGURE 12A

```
1      ssshpifhr
10     gefsvcdsvs vwvgdkttat dikgkevmvl gevninnsvf
50     kqyffetkcr dpnpvdsgcr gidskhwnsy cttthtfvka
90     ltmdgkqaaw rfiridtacv cvlsrkavrr a
```

= mature human NGF (=aa122-241 from SEQ ID NO: 4) = SEQ ID NO: 2

```
1      ya ehkshrgeys vcdseslwvt dkssaidirg hqvtvlgeik
43     tgnspvkqyf yetrckearp vkngcrgidd khwnsqckts
83     qtyvraltse nnklvgwrwi ridtscvcal srkigrt
```
= mature human NGF (= aa139-257

FIGURE 12B

SEQUENCE LISTING

```
<160> NUMBER OF SEQ ID NOS: 7

<210> SEQ ID NO 1
<211> LENGTH: 118
<212> TYPE: PRT
<213> ORGANISM: Mus musculus

<400> SEQUENCE: 1

Ser Ser Thr His Pro Val Phe His Met Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Thr Val Leu Ala Glu Val Asn Ile Asn Asn Ser Val
        35                  40                  45

Phe Arg Gln Tyr Phe Phe Glu Thr Lys Cys Arg Ala Ser Asn Pro Val
    50                  55                  60

Glu Ser Gly Cys Arg Gly Ile Asp Ser Lys His Trp Asn Ser Tyr Cys
65                  70                  75                  80

Thr Thr Thr His Thr Phe Val Lys Ala Leu Thr Thr Asp Glu Lys Gln
                85                  90                  95

Ala Ala Trp Arg Phe Ile Arg Ile Asp Thr Ala Cys Val Cys Val Leu
            100                 105                 110

Ser Arg Lys Ala Thr Arg
        115

<210> SEQ ID NO 2
<211> LENGTH: 120
<212> TYPE: PRT
<213> ORGANISM: Homo sapiens

<400> SEQUENCE: 2

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120
```

```
<210> SEQ ID NO 3
<211> LENGTH: 307
<212> TYPE: PRT
<213> ORGANISM: Mus musculus

<400> SEQUENCE: 3

Met Leu Cys Leu Lys Pro Val Lys Leu Gly Ser Leu Glu Val Gly His
1               5                   10                  15

Gly Gln His Gly Gly Val Leu Ala Cys Gly Arg Ala Val Gln Gly Ala
                20                  25                  30

Gly Trp His Ala Gly Pro Lys Leu Thr Ser Val Ser Gly Pro Asn Lys
            35                  40                  45

Gly Phe Ala Lys Asp Ala Ala Phe Tyr Thr Gly Arg Ser Glu Val His
        50                  55                  60

Ser Val Met Ser Met Leu Phe Tyr Thr Leu Ile Thr Ala Phe Leu Ile
65                  70                  75                  80

Gly Val Gln Ala Glu Pro Tyr Thr Asp Ser Asn Val Pro Glu Gly Asp
                85                  90                  95

Ser Val Pro Glu Ala His Trp Thr Lys Leu Gln His Ser Leu Asp Thr
            100                 105                 110

Ala Leu Arg Arg Ala Arg Ser Ala Pro Thr Ala Pro Ile Ala Ala Arg
        115                 120                 125

Val Thr Gly Gln Thr Arg Asn Ile Thr Val Asp Pro Arg Leu Phe Lys
130                 135                 140

Lys Arg Arg Leu His Ser Pro Arg Val Leu Phe Ser Thr Gln Pro Pro
145                 150                 155                 160

Pro Thr Ser Ser Asp Thr Leu Asp Leu Asp Phe Gln Ala His Gly Thr
                165                 170                 175

Ile Pro Phe Asn Arg Thr His Arg Ser Lys Arg Ser Ser Thr His Pro
            180                 185                 190

Val Phe His Met Gly Glu Phe Ser Val Cys Asp Ser Val Ser Val Trp
        195                 200                 205

Val Gly Asp Lys Thr Thr Ala Thr Asp Ile Lys Gly Lys Glu Val Thr
210                 215                 220

Val Leu Ala Glu Val Asn Ile Asn Asn Ser Val Phe Arg Gln Tyr Phe
225                 230                 235                 240

Phe Glu Thr Lys Cys Arg Ala Ser Asn Pro Val Glu Ser Gly Cys Arg
                245                 250                 255

Gly Ile Asp Ser Lys His Trp Asn Ser Tyr Cys Thr Thr Thr His Thr
            260                 265                 270

Phe Val Lys Ala Leu Thr Thr Asp Glu Lys Gln Ala Ala Trp Arg Phe
        275                 280                 285

Ile Arg Ile Asp Thr Ala Cys Val Cys Val Leu Ser Arg Lys Ala Thr
290                 295                 300

Arg Arg Gly
305

<210> SEQ ID NO 4
<211> LENGTH: 241
<212> TYPE: PRT
<213> ORGANISM: Homo sapiens

<400> SEQUENCE: 4

Met Ser Met Leu Phe Tyr Thr Leu Ile Thr Ala Phe Leu Ile Gly Ile
1               5                   10                  15
```

```
Gln Ala Glu Pro His Ser Glu Ser Asn Val Pro Ala Gly His Thr Ile
             20                  25                  30
Pro Gln Ala His Trp Thr Lys Leu Gln His Ser Leu Asp Thr Ala Leu
         35                  40                  45
Arg Arg Ala Arg Ser Ala Pro Ala Ala Ile Ala Ala Arg Val Ala
 50                  55                  60
Gly Gln Thr Arg Asn Ile Thr Val Asp Pro Leu Phe Lys Lys Arg
 65                  70                  75                  80
Arg Leu Arg Ser Pro Arg Val Leu Phe Ser Thr Gln Pro Pro Arg Glu
             85                  90                  95
Ala Ala Asp Thr Gln Asp Leu Asp Phe Glu Val Gly Gly Ala Ala Pro
             100                 105                 110
Phe Asn Arg Thr His Arg Ser Lys Arg Ser Ser Ser His Pro Ile Phe
             115                 120                 125
His Arg Gly Glu Phe Ser Val Cys Asp Ser Val Ser Val Trp Val Gly
 130                 135                 140
Asp Lys Thr Thr Ala Thr Asp Ile Lys Gly Lys Glu Val Met Val Leu
 145                 150                 155                 160
Gly Glu Val Asn Ile Asn Asn Ser Val Phe Lys Gln Tyr Phe Phe Glu
             165                 170                 175
Thr Lys Cys Arg Asp Pro Asn Pro Val Asp Ser Gly Cys Arg Gly Ile
             180                 185                 190
Asp Ser Lys His Trp Asn Ser Tyr Cys Thr Thr Thr His Thr Phe Val
             195                 200                 205
Lys Ala Leu Thr Met Asp Gly Lys Gln Ala Ala Trp Arg Phe Ile Arg
 210                 215                 220
Ile Asp Thr Ala Cys Val Cys Val Leu Ser Arg Lys Ala Val Arg Arg
 225                 230                 235                 240
Ala

<210> SEQ ID NO 5
<211> LENGTH: 19
<212> TYPE: DNA
<213> ORGANISM: Artificial
<220> FEATURE:
<223> OTHER INFORMATION: p75NTR primer

<400> SEQUENCE: 5
acctgccctc ctcattgca                                              19

<210> SEQ ID NO 6
<211> LENGTH: 19
<212> TYPE: DNA
<213> ORGANISM: Artificial
<220> FEATURE:
<223> OTHER INFORMATION: p75NTR primer

<400> SEQUENCE: 6
ctcccactcg tcattcgac                                              19

<210> SEQ ID NO 7
<211> LENGTH: 7
<212> TYPE: PRT
<213> ORGANISM: Homo sapiens
```

```
<400> SEQUENCE: 7

Gln Tyr Phe Phe Glu Thr Lys
1               5
```

POST-TRANSLATIONALLY MODIFIED NEUROTROPHIN ANTIBODIES

CROSS-REFERENCE TO RELATED APPLICATIONS

This application is a continuation under 35 U.S.C. §120 of U.S. patent application Ser. No. 12/374,485, filed Apr. 10, 2009 which is the U.S. national-stage of PCT/EP07/06528, filed Jul. 23, 2007; priority is also claimed to Europe 06291195.3, filed Jul. 24, 2006. The contents of these applications are incorporated by reference in their entireties.

FIELD OF THE INVENTION

The invention relates to the field of neurotrophins, and more particularly to post-translationally modified neurotrophins, as well as to their biological, biotechnological, medical, clinical, therapeutic and diagnostic applications.

BACKGROUND OF THE INVENTION

Neurotrophins, and more particularly Nerve Growth Factor (NGF), are critical for the differentiation and survival of specific neuronal populations during development, and modulate neural plasticity in the mature nervous system [1, 2]. Paradoxically, NGF has also been described as inducing apoptosis of neurons during development and eliminates damaged neurons and glial cells in pathological conditions [3, 4]. NGF has been described as a mediator of tissue inflammation and chronic pain [5], and as accumulating in several pathologies undergoing neuroinflammation [6-8].

NGF exerts its actions through two non-related transmembrane receptors, the tyrosine kinase receptor TrkA, and the p75 neurotrophin receptor ($p75^{NTR}$). TrkA is a tyrosine kinase receptor that activates well-characterized signalling pathways promoting neuronal survival, differentiation and plasticity [2, 9, 10], whereas $p75^{NTR}$ is a member of the tumor necrosis factor receptor superfamily that can act as a death receptor signalling apoptosis [4, 11]. In addition, $p75^{NTR}$ can also act as a co-receptor for Trk A, B, and C, or interact with other receptors (sortilin, Nogo-R) to modulate diverse biological effects, including survival, cytoskeleton rearrangement and axonal elongation [4, 12].

Hence, native neurotrophins, such as NGF, have been described as capable of inducing $p75^{NTR}$-dependent apoptosis.

$p75^{NTR}$ is highly expressed in motor neurons at the embryonic stage, but its expression levels gradually ends after birth [13]. Neither TrkA nor $p75^{NTR}$ are expressed by adult motor neurons, although $p75^{NTR}$ can be re-expressed following axotomy [14-16] and in pathological conditions involving motor neuron degeneration, such as amyotrophic lateral sclerosis (ALS) [17, 18]. Furthermore, $p75^{NTR}$ has been implicated in motor neuron death induced by axotomy [14, 19, 20]. Abnormal expression of $p75^{NTR}$ and NGF may contribute to adult motor neuron death observed in ALS transgenic mice overexpressing mutant Cu—Zn superoxide dismutase (SOD-1) [18, 21-25].

More recently, pro-neurotrophins have emerged as potent inducers of $p75^{NTR}$-dependent apoptosis by signalling through a complex formed by $p75^{NTR}$ and sortilin [14, 15].

For example, WO 2005/014039 expresses and follows this "pro-neurotrophin" hypothesis, without envisioning the possibility of any post-translational modification of the mature neurotrophin: see e.g., page 46 lines 24-28 of the PCT application as published, which states <<because endogenous mature NGF were found in only extremely low concentrations in the tissue extracts and nearly failed to meet the detection limit in culture media, NGF precursors (19-21, 28 and 32 kDa) are the more likely mediators of apoptosis for p75NTR-expressing motor neurons>>.

Hence, before the invention, the main hypothesis was that pro-neurotrophin, such as pro-NGF, was the endogenous factor leading to neuron apoptosis.

SUMMARY OF THE INVENTION

The inventors have identified, isolated and purified a new species of growth factor that mediates inflammation, chronic pain and neuropathology. The inventors have found that during such conditions or diseases, neurotrophins, such as NGF, react with endogenous nitrating species, such as peroxynitrite, leading to the nitration of said neurotrophins, and more particularly to the formation of nitrated tyrosine and/or tryptophan residues on said neurotrophins, and that such a nitrative modification of the neurotrophin molecule induces significant conformational changes in the native dimer, which in turn promotes the formation of high molecular weight abnormal oligomers (such as tetramers and/or octamers) that are comparable to those found in degenerating tissues.

The inventors have thus identified, isolated and purified modified neurotrophins, which have a conformation, a structure and biological activities that are strikingly different from those of native unmodified neurotrophins.

Hence, the inventors have found that such a modified neurotrophin is a key agent as an inflammatory mediator, and can play an important role in the induction of chronic pain and in neuron death in neuropathology.

The invention thus relates to such modified neurotrophins, and more particularly to nitrated neurotrophins.

The invention further relates to binders, which are compounds or compositions that are capable of binding to such modified neurotrophins, and more particularly to specific binders, which are capable of binding to at least one of such modified neurotrophins, without cross-reacting with the unmodified native neurotrophin(s).

The invention also relates to the biological, biotechnological, medical, clinical, therapeutic, diagnostic applications of such modified neurotrophins, and of such binders.

BRIEF DESCRIPTION OF THE FIGURES

FIGS. 11 and 12. NGF amino acid sequences

FIG. 11A: mouse NGF (AAA39818; SEQ ID NO:3)

FIG. 11B: human NGF (CAA37703; SEQ ID NO:4)

FIG. 12A: mature mouse NGF (SEQ ID NO:1)

FIG. 12B: mature human NGF (SEQ ID NO:2)

The Tyr (Y) and Trp (W) residues are shown in bold and underlined characters in FIGS. 12A and 12B:

- in FIG. 12A (mature mouse NGF), are shown the Trp21, Tyr52, Trp76, Tyr79, Trp99 residues of mature mouse NGF (the residue numbering being computed by reference to the sequence of the mature neurotrophin protein);
- in FIG. 12B (mature human NGF), are shown the Trp21, Tyr52, Trp76; Tyr79 and Trp99 residues of mature human NGF (the residue numbering being computed by reference to the sequence of the mature neurotrophin protein).

Figure 13:
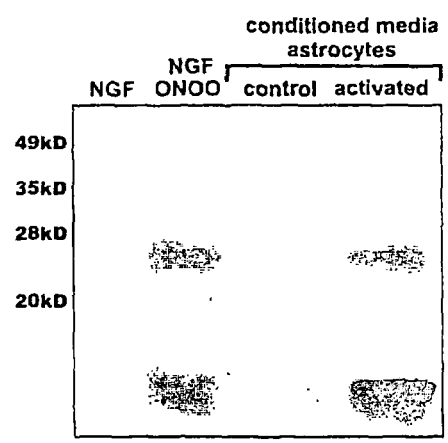

FIG. 13. Analysis by western blotting of the conditioned media from resting or stimulated astrocytes (FGF1, 10 ng/mL; and LPS, 5 microg/mL), using a specific antibody that binds to nitrated NGF, without cross-reacting with non-nitrated NGF (lane 1: non-nitrated NGF; lane 2: nitrated NGF; lane 3: conditioned media from resting astrocytes; lane 4: conditioned media from stimulated astrocytes).

Figure 14:
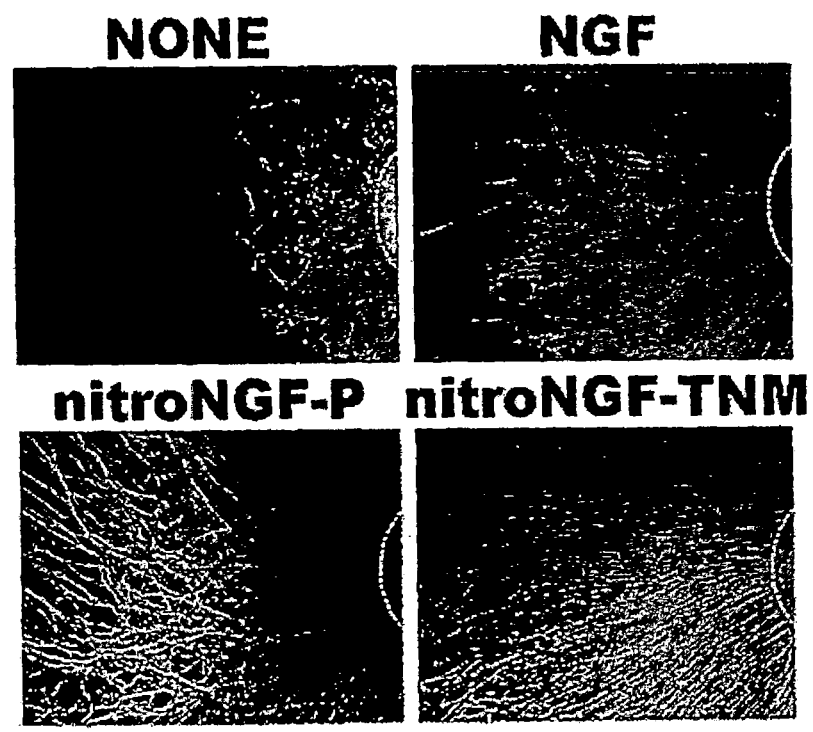

FIG. 14. Peroxynitrite increases the neurite outgrowth promoting activity of NGF.

Dorsal root ganglia explants from E15 rat embryos (that express both TrkA and $p75^{NTR}$) were cultured in Neurobasal media in the absence of trophic factors (NONE) or in the presence of NGF (100 ng/mL), NGF treated with peroxynitrite (100 ng/mL; nitroNGF-P) or NGF treated with tetranitromethane (nitroNGF-TNM). After 24 hours cultures were fixed with 4% paraformaldehyde and processed for immunofluorescence against GAP-43. Note that ganglia treated with nitroNGF exhibit increased neurite growth compared to those treated with NGF.

DETAILED DESCRIPTION

The invention describes that neurotrophins undergo post-translational modifications. To the best of the inventors' knowledge, the invention is the first description of a post-translational modification of a neurotrophin, and more particularly of NGF.

The inventors demonstrate that these post-translational modifications lead to conformationally different dimers, as well as to abnormal oligomers, such as tetramers and octamers.

Such modified neurotrophins differ from unmodified native (healthy) neurotrophins in structure, conformation, and biological activity.

Such modified neurotrophins have a pro-apoptotic effect on motor neurons, and/or a pro-neurite outgrowth effect on sensory ganglia. Furthermore, these modified neurotrophins can exert these effects at very low concentrations: the potency of a modified neurotrophin to induce and/or stimulate such effects is highly increased compared to the potency that may have (if any) the unmodified neurotrophin, from which it derives, even when such an unmodified neurotrophin is used in the presence of added exogenous nitric oxide.

The inventors further demonstrate that under in vivo conditions, these post-translational modifications notably result from the nitration of the mature neurotrophin by endogenous nitrating species, such as peroxynitrite.

Peroxynitrite (ONOO⁻), the reaction product from nitric oxide and superoxide radicals, is formed in vivo mostly in pathological conditions associated with increased production of nitric oxide.

To the best of the inventors' knowledge, it is also the first time that such modified neurotrophins are identified, isolated and purified.

In a first aspect, the invention thus relates to these modified neurotrophins, and more particularly to these nitrated neurotrophins.

Previous studies, such as Frazier et al. 1973 [52], reported that nitration of NGF by tetranitromethane (TNM) did not modify NGF biological activity, at least as assessed by induction of neurite outgrowth in sensory ganglia. The invention precisely demonstrates that, on the contrary, nitration of NGF or another neurotrophin, by a nitration agent, such as TNM and/or peroxynitrite, deeply modifies its biological activity.

Before the invention, it has never been figured out that it is a post-translational modification of neurotrophins, such as NGF (namely, nitration and/or abnormal oligomerization of NGF), that mediates the pro-apoptotic activity exerted by NGF on motor neurons. The prior art teaching only encompassed unmodified NGF and/or its precursor forms, such as pro-NGF; see e.g., Pehar et al., 2004 [25].

The post-translationally modified neurotrophins that have been identified by the inventors have a motor neuron apoptotic activity and/or a neurite outgrowth activity at very low concentrations. The potency of such a modified neurotrophin to induce and/or stimulate motor neuron apoptosis, and/or neurite outgrowth (e.g., from sensory ganglia), is highly increased compared to the potency that may be exerted (if any) by the unmodified native neurotrophin, from which it derives, even when said unmodified native neurotrophin is used in the presence of added exogenous nitric oxide.

The effect(s) of modified neurotrophins, such as a modified NGF, is(are) detectable at very low concentrations. For example, nitrated NGF significantly induces motor neuron apoptosis at concentrations as low as 1 ng/mL (cf. FIG. 2A and associated comments).

When used in association with nitric oxide, or a source of nitric oxide, the apoptotic activity of a modified neurotrophin is even further increased.

Figure 2A:
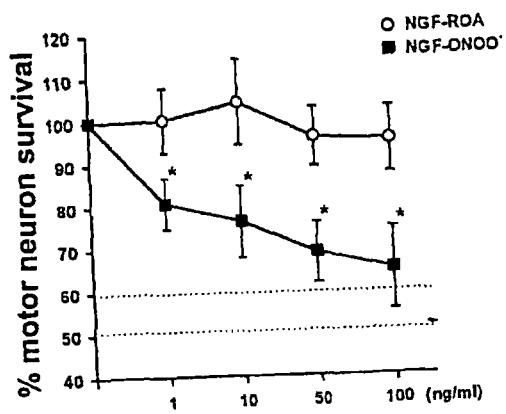
FIG. 2. Peroxynitrite treatment enhanced NGF apoptotic activity. (A) Pure motor neuron cultures maintained with GDNF (1 ng/mL) were exposed to increasing concentrations of NGF previously treated with peroxynitrite (1 mM; NGF-$ONOO^-$) or decomposed peroxynitrite (NGF-ROA). Dashed lines represent the SD of NONE (trophic factor deprivation). (B) Motor neuron cultures were exposed to NGF (10 ng/mL) previously treated with the indicated peroxynitrite concentrations. Dashed lines represent the SD of NONE (trophic factor deprivation). (C) Motor neuron cultures were treated with increasing concentrations of NGF-ROA or NGF-$ONOO^-$ (1 mM) in the presence of the nitric oxide donor DETA-NON-Oate (10 µM, NO). Dashed lines represent the SD of NONE (trophic factor deprivation). (D) Motor neuron cultures were exposed to NGF (100 ng/mL), BSA (100 ng/mL), FGF-1 (10 ng/mL) or FGF-2 (10 ng/mL) previously treated with peroxynitrite (1 mM; black bars, ONOO⁻) or decomposed peroxynitrite (1 mM; white bars, ROA). Dashed lines represent SD of GDNF. Motor neuron survival was determined 48 h after treatment. Data are expressed as percentage of GDNF, mean±SD. *Significantly different from GDNF (p≤0.05).
Figure 2B:
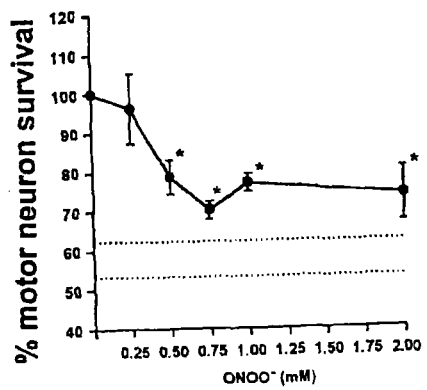
Figure 2C:
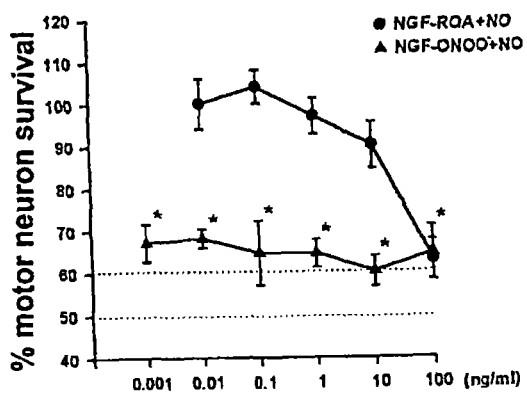

For example, nitrated NGF used together with nitric oxid (NGF-ONOO⁻+NO) significantly induces motor neuron loss at only 1 pg/mL (cf. FIG. 2C and associated comments). Nitration of NGF by peroxynitrite in vitro increased the potency of NGF to induce apoptosis of motor neurons by 10,000-fold in the presence of nitric oxide.

Figure 2D:
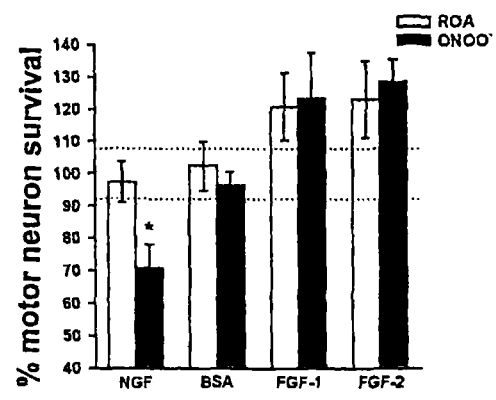

Furthermore, the activities exerted by a nitrated neurotrophin on motor neuron apoptosis, and/or on neurite outgrowth from sensory ganglia, appear to be rather specific, as nitrated growth factors other than nitrated neurotrophins, such as nitrated FGF, do not exert any apoptotic effect on motor neurons (e.g., nitro-FGF-1, nitro-FGF-2; cf. FIG. 2D and associated comments).

The invention thus relates to modified neurotrophins, which are highly potent inducers and/or stimulators of motor neuron apoptosis and/or of neurite outgrowth. These modified neurotrophins have been isolated, identified and characterized by the inventors.

The modified neurotrophins can be characterized by the fact that at least one residue selected from their Tyr and Trp residues comprises at least one nitro group.

The modified neurotrophins can alternatively or additionally be characterized by the fact that they are obtainable by post-translational nitrative modification of a native neurotrophin, by addition on said native neurotrophin of at least one nitro group on at least one residue selected from Tyr and Trp residues, wherein said native neurotrophin is a native pro-neurotrophin or a native mature neurotrophin, preferably a native mature neurotrophin.

By native neurotrophin or native pro-neurotrophin, it is herein intended the neurotrophin or pro-neurotrophin corresponding to the naturally-occurring neurotrophin or pro-neurotrophin that is observed in a healthy mammal, or at the very least in a mammal which does not suffer from any abnormal motor neuron apoptosis. A native neurotrophin or pro-neurotrophin thus herein corresponds to the normal "healthy" neurotrophin or pro-neurotrophin. Hence, such a native neurotrophin or pro-neurotrophin is not nitrated.

The term "neurotrophin" is herein meant as the group consisting of NGF (nerve growth factor), BDNF (brain-derived neurotrophic factor), NT-3 (neurotrophin-3), NT-4 (neurotrophin-4; which is also referred to as NT-4/5, i.e., neurotrophin-4/5) and NT-6 (neurotrophin-6). In the absence of any further indication, this term encompasses mature neurotrophin, as well as pro-neurotrophin. In the present invention, preferred neurotrophins are mature neurotrophins.

The invention also relates to the conservative fragments and to conservative variants.

A conservative fragment is a fragment which has retained at least one nitro group on at least one residue, preferably on at least one residue selected from Tyr and Trp residues. It has also retained a capacity of inducing and/or stimulating motor neuron apoptosis and/or neurite outgrowth.

A conservative variant derives from a modified neurotrophin or from a conservative fragment of the invention, by at least one amino acid substitution and/or deletion and/or addition, but has retained at least one nitro group on at least one residue, preferably on at least one residue selected from Tyr and Trp residues. Said conservative variant has also retained a capacity of inducing and/or stimulating motor neuron apoptosis and/or neurite outgrowth.

In the present application, unless otherwise stated, the term "modified neurotrophin" or "nitrated neurotrophin" encompasses a modified neurotrophin of the invention, as well as any conservative fragment thereof, as well as any conservative variant of such a modified neurotrophin or of such a conservative fragment.

Nitrated neurotrophins of the invention may be obtained by contacting a native neurotrophin or a native pro-neurotrophin with a nitration agent.

A conservative fragment of the invention can be obtained:
by cleavage of a modified neurotrophin of the invention, or
by contacting fragments of a native neurotrophin or of a native pro-neurotrophin with a nitration agent,
whereby a population of candidate fragments is obtained, and
by selection among said population of candidate fragments of a fragment, which has retained at least one nitro group on at least one residue, preferably on at least one residue selected from Tyr and Trp residues, and which has a capacity of inducing and/or stimulating motor neuron apoptosis and/or neurite outgrowth.

A conservative variant of the invention can be obtained:
by substitution and/or deletion and/or addition of at least one amino acid of a modified neurotrophin of the invention or of a conservative fragment of the invention, or by contacting a variant of a native neurotrophin, or of a native pro-neurotrophin, or of a native neurotrophin fragment, or of a native pro-neurotrophin fragment, with a nitration agent,
whereby a population of candidate variant(s) is obtained, and
by selection among this population of candidate variant(s) of a variant that has retained at least one nitro group on at least one residue, preferably on at least one residue selected from Tyr and Trp residues, and that has a capacity of inducing and/or stimulating motor neuron apoptosis and/or neurite outgrowth.

Any nitration agent that the skilled person may find appropriate can be used. One or several nitration agent(s) may be used. The nitration agent(s) being used are agent(s), which comprise(s) at least one nitro group, and which are capable of inducing the addition of said at least one nitro group on a neurotrophin protein, or a fragment or variant thereof, preferably on at least one residue selected from the Tyr and Trp residue(s) of said neurotrophin, or fragment or variant thereof. Preferably, said nitration agent is tetranitromethane and/or peroxynitrite.

The neurotrophin to be nitrated (or the fragment or variant thereof) may originate from any source that the skilled person may find appropriate. It may be a natural peptide, polypeptide or protein, or a fragment of a natural polypeptide or protein, or a recombinant peptide, polypeptide or protein, or a synthetic peptide or polypeptide. Any method of peptide or polypeptide synthesis that is known to the skilled person can be used. Examples of synthesis methods, such as the Merrifield solid phase synthesis, can e.g., be found in <<Solid Phase Peptide Synthesis >> (J. M. Steward & J. D. Young, 1969, Ed. W. H. Freeman Co., San Francisco), or in <<Peptide synthesis >> (M. Bodansky et al. 1976, John Wiley & Sons, 2nd Edition).

Natural sources of neurotrophin notably include astrocytic cells, e.g., type II astrocytic glial cells.

Neurotrophins are also commercially available, such as murine NGF, which is available from Harlan (Indianapolis; USA).

Recombinant neurotrophins, or neurotrophin fragments or variants, may also be produced by the person of average skill in the art, e.g., by infecting and/or transfecting and/or transforming appropriate host cells (e.g., fibroblast cells) with a cDNA that encodes said neurotrophin or fragment or variant, under conditions appropriate for the expression of the protein or polypeptide or peptide encoded by this cDNA. For example, the production of recombinant human NGF has been described in Johnson et al. 1986 (Cell 47(4):545-554; production from mouse fibroblasts), in Allen et al. 2001 (J. Biochem. Biophys. Methods. 47:239-255; production from baculovirus and insect cell systems), in Rattenholl et al. 2001 (Eur. J. Biochem. 268:3296-3303; production from a bacterial system).

Said neurotrophin (or a conservative fragment or variant thereof) is contacted by said nitration agent under conditions (more particularly, under pH and duration conditions) that are appropriate for said nitration agent to induce the addition of at least one nitro group on at least one of the Trp and Tyr residues of said neurotrophin, or fragment or variant.

The capacity of inducing and/or stimulating motor neuron apoptosis and/or neurite outgrowth can be assessed by any means that are available to the skilled person. For example, the capacity of inducing and/or stimulating neurite outgrowth can be assessed by exposing sensory ganglia to said nitrated neurotrophin, or fragment or variant thereof, and determining the level of neurite outgrowth, so as to determine whether said exposure to said nitrated neurotrophin (or fragment or variant thereof) induces or increases the number of neuritis outgrowing from said sensory ganglia. To determine whether the number of neurites increases, upon exposure to said nitrated neurotrophin (or fragment or variant thereof), compared to control conditions, a statistically significant increase of the number of neuritis may be observed.

For example, the capacity of inducing and/or stimulating motor neuron apoptosis can be assessed by exposing motor neurons to said nitrated neurotrophin, or fragment or variant thereof, and counting the non-apoptotic cells, e.g., the cells that display intact neurites longer than 4-cell bodies in diameter, and/or the apoptotic cells, so as to determine whether said exposure to said nitrated neurotrophin (or fragment or variant thereof) induces or increases the number of motor neurons undergoing apoptosis. To determine whether the number of non-apoptotic cells decreases and/or whether the number of apoptotic cells increases, upon exposure to said nitrated neurotrophin (or fragment or variant thereof), compared to control conditions, a statistically significant decrease of the number of non-apoptotic cells and/or a statistically significant increase of the number of apoptotic cells, respectively, may be observed.

For such determinations, appropriate controls that does not comprise the exposure to said nitrated neurotrophin (or fragment or variant thereof) are usually made, such as by placing comparable motor neurons or sensory ganglia in comparable experimental conditions, but without exposure to said nitrated neurotrophin (or fragment or variant thereof), or by exposure to a control neurotrophin which has been submitted to a decomposed nitration agent (e.g., decomposed peroxynitrite) and which is added in reverse order addition. Details of illustrative culture and experimental conditions can be found described in the examples below (see for example FIG. 2A and comments relating thereto, as well as the paragraph entitled "purified motor neuron cultures").

The term "statistically significant" or "significantly" is herein used in its usual meaning in the field of statistics (e.g., t test, z test, chi squared value, or F ratio, etc.), i.e., for comparing a value to another one, and determining whether these values differ from each other. The term "statistically significant" or "significantly" hence encompasses the fact that the skilled person may take into account the standard deviation (if any), which measures the amount of spread of data in a frequency distribution. The desired p value is usually set at an alpha level of 5%, or at the more stringent alpha level of 1%.

The monomers of each of the neurotrophins share a number of chemical characteristics, including similar molecular sizes (13.2-15.9 kDa, and exceptionally 21 kDa for NT-6), primary sequence identities that approach or exceed 50%, isoelectric points in the range 9-10, and six conserved half-cystines in the same conserved positions that give rise to three intrachain disulfide bonds. These three disulfide bonds form a characteristic cystine knot (see FIG. 1). Preferably, said neurotrophin is NGF or BDNF. Most preferably, said neurotrophin is NGF.

Amino acid sequences of murine NGF and human NGF are shown in FIGS. 11A, 12A (murine NGF) and 11B and 12B (human NGF).

Preferably, said neurotrophin is a human neurotrophin, most preferably a human NGF.

The product of the nitration reaction may comprise unreacted compounds and/or by-products. If desired or necessary, said post-translational nitrative modification is followed by separation and/or isolation of the nitrated neurotrophin from unreacted compounds and/or by-products.

The product of the nitration reaction may comprise several monomer/oligomer species of the nitrated neurotrophin. If desired or necessary, said post-translational nitrative modification is followed by separation and/or isolation of each of these different monomer/oligomer species, whereby these species are separated and/or isolated from each other.

Said separation and/or isolation can e.g., be performed by HLPC chromatography, and/or by mass spectrometry of HPLC eluent fractions (electrospray time-of-flight mass spectrometry), whereby each monomer or oligomer species is obtainable in a pure form.

Methods that may be appropriated to obtain one single monomer/oligomer species in a pure form may include, liquid separation using size exclusion, ion exchange, immunoaffinity or reverse phase chromatography. Electrophoresis in non-denaturalizing conditions and immunoprecipitation may also be applied.

Said nitration of neurotrophin can be performed by contacting said neurotrophin with a nitration agent, such as peroxynitrite and/or tetranitromethane, under conditions enabling the addition of at least one nitro group, preferably on at least one Tyr or Trp residue.

For example, said nitration can be performed in 50 mM sodium phosphate buffer, pH 7.4, containing 20 mM sodium bicarbonate.

Said neurotrophin can for example be at a concentration of 0.2 to 1 mg/mL.

Said neurotrophin may e.g., be subjected to at least one bolus addition (1 microL) of a peroxynitrite solution at a concentration of 0.25 to 2 mg/mL in a 0.01M NaOH solution. Several bolus additions may be performed, e.g., up to ten bolus addition (1 microL each) of said peroxynitrite solution.

Successive bolus additions of peroxynitrite cause a dose dependent appearance of oligomers of increasing mer-numbers. It can be observed e.g., on SDS-PAGE by a dose dependent appearance of three high molecular weight species (see FIG. 4A for nitrated NGF), or by HPLC size-exclusion chromatography coupled to real-time multi-angle light scattering (MALS) (33.2±0.6 kDa for the nitrated NGF dimer; 68.5±3.5 kDa for the nitrated NGF tetramer; 68.5±3.5 kDa for the nitrated NGF octamer; see FIG. 4B). Surprisingly, the peroxynitrite-treated NGF dimer elutes before the native NGF dimer (as assessed by HPLC size-exclusion chromatography coupled to MALS analysis), reflecting the existence of conformational changes. This dose-dependent appearance of oligomers of increasing mer-numbers is accompanied by a progressive decrease in staining intensity of native NGF.

Figure 4A:
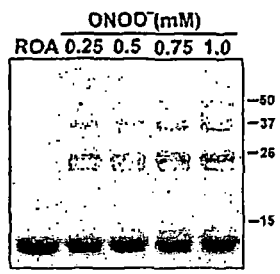
FIG. 4. Peroxynitrite induced NGF oligomerization and nitration. (A) SDS-PAGE showing the formation of high molecular weight species of NGF following treatment with increased concentrations of peroxynitrite (ONOO⁻; 0.25 mM to 1 mM). As a control, NGF was treated with decomposed peroxynitrite (1 mM; ROA). NGF was treated with peroxynitrite at a concentration of 0.2 mg/mL. 10 μg of protein were applied in each lane and electrophoretic separation was performed in 15% polyacrylamide gels under denaturing and reducing conditions. Figure shows a representative gel stained with Coomasie Blue. (B) NGF treated with 1 mM peroxynitrite (NGF-ONOO⁻) or its degradation products (NGF-ROA) was analysed by size-exclusion chromatography coupled to real-time multi-angle light scattering (MALS). The absolute molar mass versus time (or volume) of elution was superimposed with the signals from the 90° LS detector. NGF-ROA (blue) eluted as a single peak with a mass corresponding to the dimer (33.0±1.2 KDa). In contrast, NGF-ONOO⁻ eluted as three peaks corresponding to dimer (33.2±0.6 KDa, 85% of the protein), tetramer (68.5±3.5 KDa, 13%) and octamer (125.0±10.0 KDa, 2%). (C) Western blot showing increase immunoreactivity for nitrotyrosine. 100 ng of NGF treated as in (A) was analysed by immunoblotting using anti-nitrotyrosine (anti-NitroTyr) polyclonal antibodies. After stripping the membrane was developed with anti-NGF polyclonal antibodies.
Figure 4B:
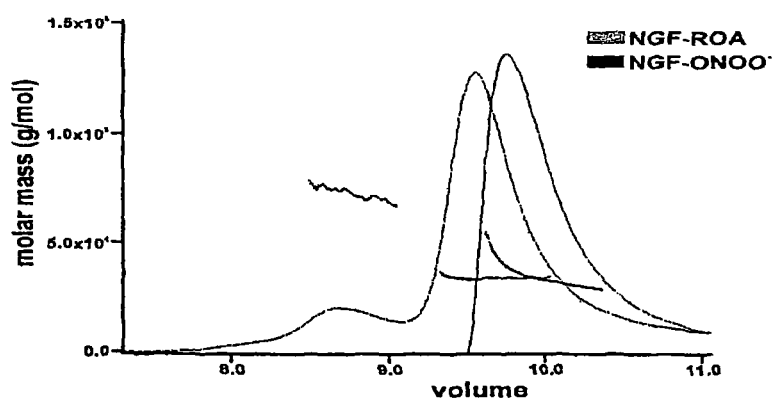
Figure 4C:
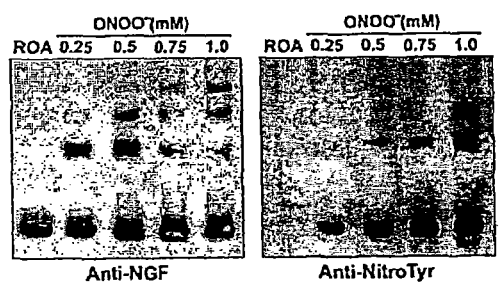

Successive bolus additions of peroxynitrite also induce a dose-dependent nitration of the contacted neutrophin (see FIG. 4C for nitrated NGF).

Figure 5A:
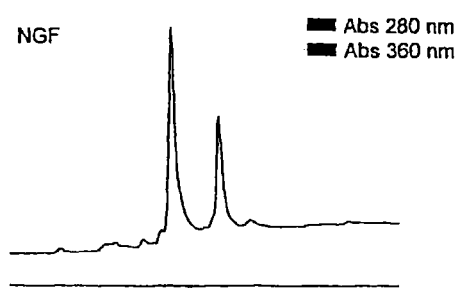
FIG. 5A). Mass signal at 13,168 Da corresponded to double nitrated Chain A lacking the C-terminal arginine residue. Deconvoluted spectra of the eluent at 39.9 minutes showed similar mass shifts for Chain B. (C) Q-T of mass spectrum of trypsin-digested eluent at 37.9 minutes indicated nitration of Tyr52 and Tyr79. Analysis of eluent at 39.9 minutes indicated the same modification on Chain B. (D) SDS-PAGE showing the formation of high molecular weight species of NGF following the treatment with TNM (NGF-TNM). 100 ng of protein were analysed in each lane and electrophoretic separation was performed in 15% polyacrilamide gels under denaturing and reducing conditions. The figure shows a representative gel silver stained.

Native NGF elutes as two peaks by reverse-phase HPLC, at 36.3 and 38.1 min (see FIG. 5A), corresponding to NGF chain A and NGF chain B.

Nitrated NGF elutes later, for example at 38.6 min or slightly later, due to the presence of NGF species of increased molecular weights.

Hence, in addition to demonstrating that neurotrophins undergoes post-translational modifications, the inventors demonstrate that these post-translation modifications notably result from nitration, and more particularly from tyrosine nitration. Nitration was not the sole possibility of chemical modification that could account for such post-translational modifications.

Indeed, nitration of tyrosine is not the sole oxidative modification of tyrosine that is known to alter the biological activity of a protein: other oxidative modifications in tyrosine are known, such as chlorination, bromination, and hydroxylation to 3-chloro, 3-bromo- or 3-hydroxytyrosine (which are promoted with inflammatory conditions).

Other oxidative processes triggered by reactive nitrogen species such as thiol oxidation, disruption of iron-sulfur clusters and oxidation of transition metal centers can in many cases be more relevant than nitration in the promotion of cell/dysfunction/death.

Furthermore, the role of peroxynitrite in biological nitration has been recently questioned (Pfeiffer et al. 2000 J. Biol. Chem. 275:6346-6352; Thomas et al. 2002 Proc. Natl. Acad. Sci. USA 99:12691-12696).

Moreover, the invention describes not only the nitration of tyrosine residues, but also the nitration of other residues such as tryptophan (as well as, for some neurotrophins, the oxidation of methionine). The invention further describes a conformational change in the neurotrophin molecule, which leads to conformationally-different nitrated dimers, as well as to abnormal oligomerization (formation of e.g., tetramer and octamer species).

Most preferably, an isolated form of modified neurotrophin is in a molecular configuration that does not impede its pro-apoptotic activity and/or its pro-neurite outgrowth activity.

Figure 5B:
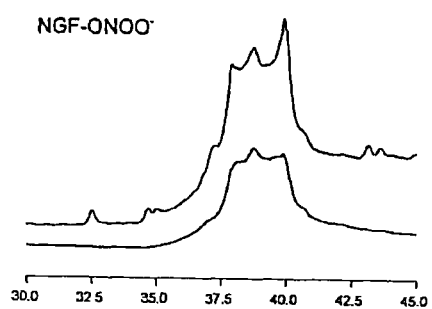
FIG. 5. Reverse-phase HPLC chromatograms of native (A) and peroxynitrite-treated (B) NGF. Native NGF eluted as two peaks at 36.3 and 38.1 minutes. Peroxynitrite-treatment (1 mM) led to an incomplete separation of several products. Nonionized nitrotyrosine absorbs at 360 nm. Peroxynitrite-treated NGF had increased absorbance at 360 nm (B) however no absorbance at 360 nm was observed in the native NGF chromatogram (A).

The product obtained after nitration of the neurotrophin (or the neurotrophin fragment or variant) can be isolated from the other components of the reaction mixture, e.g., by reverse-phase HPLC chromatography (see e.g., FIG. 5B for nitrated NGF). The eluent(s) that is(are) thus obtained may comprise one single nitrated neurotrophin oligomer species, or a mixture of nitrated neurotrophin oligomers, but may be deprived of any other compound other than nitrated neurotrophin.

If desired, such an eluent, or such eluents, may be further purified, e.g., by HPLC chromatography, to isolate the different oligomer species from each other, or at least to isolate a certain species mixture from another species or species mixture. The eluent(s) can be formulated in a form other than a liquid form, e.g., in a solid form. Techniques that are appropriate for obtaining a solid state formulation of a product that is initially available in a liquid state, without loosing the structure and conformation of the product, are known to the skilled person. Such a technique may e.g., comprises membrane separation and/or evaporation and/or crystallization and/or freeze concentration.

Preferably, an isolated form of modified neurotrophin does not comprise any non-nitrated pro-neurotrophin and/or any non-nitrated mature neurotrophin.

It preferably does not comprise any un-reacted neurotrophin, such as non-nitrated NGF dimer, nor any remaining nitration agent. Advantageously, it does not comprise any nitrated and/or non-nitrated pro-neurotrophin (pro-NGF, pro-BDNF, pro-NT-3, pro-NT-4). It does more particularly not comprise any nitrated and/or non-nitrated pro-NGF (many, if not all of the commercially-available NGF products are believed to be in fact a mixture of mature NGF and of pro-NGF).

Most preferably, it is in a substantially pure form (as defined below), more preferably in a pure form, which does not contain any compound other than nitrated neurotrophin monomer(s) and/or oligomer(s).

An "isolated" protein is a protein, which is substantially separated from other components, which naturally accompany it, e.g., proteins and flanking genomic sequences from the originating species, and which is substantially separated from other chemicals or compounds that may be present in, or formed during the protein synthesis and/or nitration reactions. The term "isolated" embraces naturally-occurring proteins or polypeptides, as well as chemically-synthetised proteins or polypeptides, and proteins or polypeptides synthetised by heterologous systems.

"Substantially pure" typically means that the protein is isolated from other compounds, such as contaminating proteins, nucleic acids, or other biological compounds derived from the original source organism, or from chemicals or compounds that are present in, or formed during, the protein synthesis and/or the nitration reactions. Purity, or "isolation", may be assayed by standard methods, typically by weight, and will generally be at least about 70% pure, more generally at least about 80% pure, often at least about 85% pure, more often at least about 90% pure, preferably at least about 95% pure, more preferably at least about 98% pure, and in most preferred embodiments, at least 99% pure. Carriers or excipients will often be added, or the formulation may be sterile and/or comprise buffer components.

A substantially pure molecule includes isolated forms of the molecule. An isolated protein will generally be a homogeneous composition of molecules, but will, in some embodiments, contain minor heterogeneity. This heterogeneity is typically found at the polymer ends or portions not critical to a desired biological function or activity.

A modified neurotrophin of the invention can consist of a monomer, or of an oligomer, such as a dimer, a trimer, a tetramer, a pentamer, a hexamer, a heptamer, an octamer. One of the preferred modified neurotrophins of the invention is in the form of a monomer, or of a dimer, or of tetramer, or of a hexamer, or of an octamer.

Alternatively, a modified neurotrophin of the invention may consist of at least two different oligomer species, e.g., at least three different oligomer species. A modified neurotrophin of the invention may thus consist of at least two, e.g. at least three, different oligomer species selected from the group consisting of dimer, trimer, tetramer, pentamer, hexamer, heptamer, octamer.

One of the preferred modified neurotrophins of the invention consists of at least two different oligomer species selected from dimer, tetramer and octamer. One of the preferred modified neurotrophins of the invention may thus consist of two oligomer species, such as dimer and tetramer, or dimer and octamer, or tetramer and octamer. Other preferred neurotrophins of the invention may thus consist of three oligomer species, such as dimer, tetramer and octamer. Still other preferred neurotrophins of the invention may thus consist of four different oligomer species, such as dimer, tetramer, hexamer and octamer.

A modified neurotrophin of the invention can be in a solid form, or in a liquid form.

A neurotrophin, such as NGF, BDNF, NT3, NT-4, has a dimeric structure consisting of two non-covalently linked monomers. When such a dimeric structure is subjected to nitration, nitration of at least one of the monomer, preferably of the two monomers, take place by addition of at least one nitro group on at least one residue, preferably selected from the Tyr and Trp residues.

Hence, when the post-translationally modified product is in solution, aggregates of modified neurotrophin dimers may form, said aggregates being in dynamic mixture, wherein the different oligomer species may reach equilibrium between each other, to form a mixture of at least two different oligomer structures selected from dimer(s), tetramer(s), hexamer(s), octamer(s).

Said modified neurotrophin may thus be in the form of an oligomer mixture consisting of at least two different oligomer structures selected from dimer, tetramer, hexamer and octamer structures, preferably from dimer, tetramer, and octamer structures.

Dependent on the particular nitration conditions and/or of the particular nitration agent being used, the resulting product may nevertheless consist of a single oligomer species. For example, when the concentration of neurotrophin starting material is low, the resulting modified neurotrophin product may consist of a single species of nitrated neurotrophin oligomer, notably of a single species of nitrated neurotrophin dimer. For example, when NGF is used at a concentration of 0.2-0.4 mg/mL as starting material, the product resulting from nitration (e.g., by peroxynitrite and/or tetranitromethane) may consist of a single species of nitrated NGF dimer. Such a modified neurotrophin dimer not only differs from the native (healthy) NGF dimer by the presence of at least one nitro group, but also by a different molecular conformation. It is evidenced, for example, by HPLC size-exclusion chromatography coupled to real-time multi-angle light scattering (MALS) analysis, notably for the modified NGF dimer (see FIG. 4B). The modified neurotrophin dimer further shows a biological activity that is drastically different from the one of the unmodified native neurotrophin dimer from which it derives, as the modified neurotrophin dimer is capable of inducing and/or stimulating the apoptosis of motor neurons and/or the outgrowth of neuritis, whereas the unmodified native neurotrophin dimer does not show such an activity, or only at a very low level, which is significantly inferior to the one observed with the nitrated neurotrophin dimer. For example, the nitrated NGF dimer of the invention has an apoptotic activity that is about 10,000 fold higher than the one of the unmodified native NGF dimer from which it derives.

Said neurotrophin, from which the modified neurotrophin derives, can be BDNF, NT-3, NT-4/5 and/or NT-6. Preferably, it is mature BDNF, mature NT-3, mature NT-4/5 or mature NT-6.

Alternatively, said neurotrophin, from which the modified neurotrophin derives, can be NGF. Preferably, it is mature NGF.

NGF is a homodimer of approximately 27 kDa [38, 39]. The mouse NGF monomer has 118 amino acids, although shorter chains truncated at both N- and C-termini were also identified [38, 40]. Mouse NGF contains two tyrosine residues at positions 52 and 79 (see FIG. 1) [41]. Conserved in all members of the neurotrophin family, Tyr52 participates in hydrophobic contacts at the dimer interface and is also engaged in $p75^{NTR}$ binding [39, 42]. Site-directed mutagenesis studies revealed the structural importance of this tyrosine residue in determining a stable protein conformation [43]. On the other hand, Tyr79 is conserved in most NGFs, but not in other members of the neurotrophin family [41]. In mouse NGF, this tyrosine makes contact with residues of the same protomer and could also interact with the N-terminus of the second protomer [39]. Since these tyrosine residues are highly conserved, peroxynitrite modification of these residues has important consequences in NGF biological activity.

Illustrative sequences of a mouse NGF and of a human NGF are shown in FIGS. 11A and 11B, respectively.

The sequences of a mature mouse NGF and of a mature human NGF are shown in FIGS. 12A and 12B, respectively.

In what follows, reference is made to specific NGF residues, more particularly to specific Tyr and Trp residues. These residues are identified by their amino acid position, such as e.g., Tyr52 or Trp99. Residue positions are herein computed by reference to the sequence of the mature protein, e.g. for mouse NGF, by reference to the sequence of SEQ ID NO:1 that is shown in FIG. 12A, or for human NGF, by reference to the sequence of SEQ ID NO:2 that is shown in FIG. 12B.

FIG. 12A shows the 3 Trp residues and the 2 Tyr residues that are contained in mouse NGF (Trp21, Tyr52, Trp76, Tyr79, Trp99).

FIG. 12B shows the 3 Trp residues and the 2 Tyr residues that are contained in human NGF (Trp21, Tyr52, Trp76; Tyr79, Trp99).

Advantageously, a modified neurotrophin of the invention is a nitrated NGF, wherein at least one residue selected from Tyr and Trp residues comprises at least one nitro group.

Said nitrated NGF can be a nitrated NGF protomer in a pure form, e.g., a nitrated NGF chain A, or a nitrated NGF chain B (chain B lacks the eight N terminal residues present in chain A).

Said nitrated NGF can be a nitrated NGF oligomer of nitrated NGF chain A and/or nitrated NGF chain B, in a pure form.

Such a nitrated NGF oligomer can be a nitrated NGF dimer (consisting of two nitrated NGF chains A, or of one nitrated chain A and one nitrated NGF chain B, or of two nitrated chains B). Please note that the peroxynitrite-treated NGF dimer elutes before the native NGF dimer (as assessed by HPLC size-exclusion chromatography coupled to MALS analysis), reflecting the existence of conformational changes (see FIG. 4B).

Such a nitrated NGF oligomer can be a nitrated NGF trimer, a nitrated NGF tetramer, a nitrated NGF pentamer, a nitrated NGF hexamer, a nitrated NGF heptamer, a nitrated NGF octamer. It preferably is selected from the group consisting of a nitrated NGF dimer, a nitrated NGF tetramer, a nitrated NGF hexamer, a nitrated NGF octamer. More preferably, it is selected from the group consisting of a nitrated NGF dimer, a nitrated NGF tetramer, a nitrated NGF octamer.

As above-mentioned, said nitrated NGF oligomer can be in the form of an oligomer mixture, such as e.g., an oligomer mixture consisting of at least two different oligomer species selected from dimer, tetramer, hexamer and octamer species, most preferably an oligomer mixture consisting of at least two different oligomer species selected from dimer, tetramer and octamer species, more preferably an oligomer mixture consisting of the dimer and the tetramer and the octamer species.

Said at least one residue selected from Tyr and Trp residues that comprises at least one nitro group can be a Tyr residue, e.g., Tyr52 or Tyr79 of murine NGF, or Tyr52 or Tyr79 of human NGF, or any equivalent residue from other species. If said neurotrophin is a mouse NGF (SEQ ID NO: 1), said at least one Tyr residue is preferably selected from the Tyr52 and the Tyr79 residues of mouse NGF (see FIG. 12A). More preferably, said at least one Tyr residue is the Tyr52 residue of mouse NGF.

If said neurotrophin is a human NGF (SEQ ID NO: 2), said at least one Tyr residue is preferably selected from the Tyr52, Tyr79 residues of human NGF (see FIG. 12B). More preferably, said at least one Tyr residue is the Tyr52 residue of human NGF.

Said at least one residue selected from Tyr and Trp residues that comprises at least one nitro group can be a Trp residue, e.g., Trp99 or Trp21 or Trp76 of mouse NGF, or Trp99 or Trp21 or Trp76 of human NGF, or any equivalent residue from other species.

The number of Tyr and Trp residues of said neurotrophin that bear a nitro group (at least one nitrogroup on each of said residues) can be of at least two, at least three, at least four, at least five, at least six, at least seven, at least eight, or at least nine.

All the Tyr and Trp residues of said neurotrophin may bear at least one nitrogroup.

If said neurotrophin is a mouse NGF, said at least two Tyr residues preferably are the Tyr52 and the Tyr79 residues of mouse NGF (see FIG. 12A).

If said neurotrophin is a human NGF, said at least two Tyr residues preferably are the Tyr52 and the Tyr79 residues of human NGF (see FIG. 12B).

If said neurotrophin is a mouse NGF, said at least one Trp residue is preferably selected from the Trp99, Trp21 and Trp76 residues of mouse NGF (see FIG. 12A). More preferably, said at least one Trp residue is the Trp99 or Trp21 residue of mouse NGF. Most preferably, said at least one Trp residue is the Trp99 residue of mouse NGF.

If said neurotrophin is a human NGF, said at least one Trp residue is preferably selected from the Trp21, Trp76, Trp99 residues of human NGF (see FIG. 12B). More preferably, said at least one Trp residue is the Trp21 or Trp99 residue of human NGF. Most preferably, said at least one Trp residue is the Trp99 residue of human NGF.

If said neurotrophin is a mouse NGF, said at least two Trp residues are preferably selected from the Trp99, Trp21 and Trp76 residues of mouse NGF (see FIG. 12A). More preferably, said at least two Trp residues are the Trp99 and the Trp21 residues of mouse NGF.

If said neurotrophin is a human NGF, said at least two Trp residues are preferably selected from the Trp21, Trp76, Trp99 residues of human NGF (see FIG. 12B). More preferably, said at least two Trp residues are the Trp21 and Trp99 residues of human NGF.

If said neurotrophin is a mouse NGF, said at least three Trp residues preferably are the Trp99, Trp21 and Trp76 residues of mouse NGF (see FIG. 12A).

If said neurotrophin is human NGF, said at least three Trp residues preferably are the Trp21, Trp76, Trp99 residues of human NGF (see FIG. 12B).

When the number of Tyr and Trp residues that bear a nitro group is of at least two or higher, these residues can be at least one Tyr residue and at least one Trp residue (at least one nitrogroup on each of said residues).

If said neurotrophin is a mouse NGF, said at least one Trp residue is preferably selected from the Trp99, Trp21 and Trp76 residues of mouse NGF (see FIG. 12A). More preferably, said at least one Trp residue is the Trp99 or Trp21 residue of mouse NGF. Most preferably, said at least one Trp residue is the Trp99 residue of mouse NGF.

If said neurotrophin is a mouse NGF, said at least one Tyr residue is preferably selected from the Tyr52 and the Tyr79 residues of mouse NGF (see FIG. 12A). More preferably, said at least one Tyr residue is the Tyr52 residue of mouse NGF. All combinations of these Tyr and Trp residues are encompassed by the present application. More preferably, said at least one Trp residue is the Trp99 or the Trp21 residue of mouse NGF, and said at least one Tyr residue is the Tyr52 residue of mouse NGF.

TABLE 1 illustrative combinations of mouse NGF Tyr and Trp residues

| Mouse NGF | Trp21 | Trp76 | Trp99 |
|---|---|---|---|
| Tyr52 | x | x | x |
| Tyr79 | x | x | x |

If said neurotrophin is a human NGF, said at least one Trp residue is preferably selected from the Trp21, Trp76, Trp99 residues of human NGF (see FIG. 12B). More preferably, said at least one Trp residue is the Trp21 or Trp99 residue of human NGF. Most preferably, said at least one Trp residue is the Trp99 residue of mouse NGF.

If said neurotrophin is a human NGF, said at least one Tyr residue is preferably selected from the Tyr52, Tyr79 residues of human NGF (see FIG. 12B). More preferably, said at least one Tyr residue is the Tyr52 residue of human NGF.

All combinations of these Tyr and Trp residues are encompassed by the present application. More preferably, said at least one Trp residue is the Trp99 or the Trp21 residue of human NGF, and said at least one Tyr residue is the Tyr52 residue of human NGF.

TABLE 2 illustrative combinations of human NGF Tyr and Trp residues

| Human NGF | Trp21 | Trp76 | Trp99 |
|---|---|---|---|
| Tyr52 | X | X | X |
| Tyr79 | X | X | X |

A modified neurotrophin of the invention may comprise at least one Tyr and at least two Trp residues that bear a nitro group (at least one nitrogroup on each of said residues).

If said neurotrophin is a mouse NGF, said at least two Trp residues are preferably selected from the Trp99, Trp21 and Trp76 residues of mouse NGF (see FIG. 12A). More preferably, said at least two Trp residues are the Trp99 and Trp21 residues of mouse NGF.

If said neurotrophin is a mouse NGF, said at least one Tyr residue is preferably selected from the Tyr52 and the Tyr79 residues of mouse NGF (see FIG. 12A). More preferably, said at least one Tyr residue is the Tyr52 residue of mouse NGF. All combinations of these Tyr and Trp residues are encompassed by the present application. More preferably, said at least two Trp residues are the Trp99 and the Trp21 residues of mouse NGF, and said at least one Tyr residue is the Tyr52 residue of mouse NGF.

If said neurotrophin is a human NGF, said at least two Trp residues are preferably selected from the Trp21, Trp76, Trp99 residues of human NGF (see FIG. 12B).

More preferably, said at least two Trp residues are the Trp21 and Trp99 residues of human NGF.

If said neurotrophin is a human NGF, said at least one Tyr residue is preferably selected from the Tyr52, Tyr79 residues of human NGF (see FIG. 12B). More preferably, said at least one Tyr residue is the Tyr52 residue of human NGF.

All combinations of these Tyr and Trp residues are encompassed by the present application. More preferably, said at least two Trp residues are the Trp99 and the Trp21 residues of human NGF, and said at least one Tyr residue is the Tyr52 residue of human NGF.

A modified neurotrophin of the invention may comprise at least two Tyr and at least two Trp residues of said neurotrophin that bear a nitro group (at least one nitrogroup on each of said residues).

A modified neurotrophin of the invention may comprise at least one Tyr and at least three Trp residues of said neurotrophin that bear a nitro group (at least one nitrogroup on each of said residues).

Of course, any combination of Tyr residue number and of Trp residue number is encompassed by the present invention. For example, mouse NGF has three Trp residues and two Tyr residues (cf. FIG. 12A); and human NGF has two Tyr residues and three Trp residues (cf. FIG. 12B).

Said nitrated neurotrophin may comprise at least one Met residue that is oxidised (e.g., Met=O). If said neutrophin is mouse NGF, said at least one Met residue preferably is the Met9 residue of (mature) mouse NGF (see FIG. 12A; residue M at position 9 in SEQ ID NO:1).

A modified neurotrophin of the invention can be in a non-glycosylated form, or in a glycosylated form.

The invention also relates to binders, which are compounds or compositions that bind to at least one modified neurotrophin of the invention, more particularly to at least one nitrated neurotrophin of the invention. Nitrated neurotrophins notably comprise nitrated NGF, nitrated BDNF, nitrated NT-3, nitrated NT-4/5 and nitrated NT-6. An illustrative binder is an antibody.

The invention more particularly relates to specific binders, which specifically bind to such modified neurotrophin(s).

Specific binders of the invention notably include those compounds or compositions that bind to at least one modified neurotrophin, more particularly to at least one nitrated neurotrophin (e.g., nitrated NGF, nitrated BDNF, nitrated NT-3, nitrated NT-4/5, nitrated NT-6), without binding to the unmodified native neurotrophin from which said at least one modified neurotrophin derives (e.g., non-nitrated native NGF, non-nitrated native BDNF, non-nitrated native NT-3, non-nitrated native NT-4/5, non-nitrated native NT-6, respectively).

Such a specific binder may bind to e.g., at least two nitrated neurotrophins of the invention (e.g., nitrated NGF and nitrated BDNF), without binding to the two non-nitrated neurotrophin dimers, from which said at least two nitrated forms derive (e.g., the non-nitrated NGF and BDNF dimers).

Most preferably, a specific binder of the invention does not bind to any non-nitrated neurotrophin (it does not bind to any non-nitrated NGF, to any non-nitrated BDNG, to any non-nitrated NT-3, to any non-nitrated NT-4/5 and to any non-nitrated NT-6).

Preferably, a specific binder of the invention binds to a nitrated NGF of the invention, without binding to the non-nitrated NGF dimer, from which said nitrated NGF derives. Most preferably, such a "nitro-NGF" specific binder does not bind to any non-nitrated NGF dimer. Most preferably, such a "nitro-NGF" specific binder does not bind to any non-nitrated neurotrophin (it does not bind to any non-nitrated NGF, to any non-nitrated BDNF, to any non-nitrated NT-3, to any non-nitrated NT-4/5 and to any non-nitrated NT-6).

Such a "nitro-NGF" specific binder may nevertheless further bind to at least one nitrated neurotrophin selected from the nitrated BDNF, the nitrated NT-3, the nitrated NT-4/5 and the nitrated NT-6 of the invention.

Preferably, a binder or specific binder of the invention does not bind to glucose. It thus does preferably not comprise any functional binding site for glucose.

Preferably, a binder or specific binder of the invention modulates, most preferably inhibits or blocks, the activity of at least one of the modified neurotrophin(s) to which said binder or specific binder binds. Said binder or specific binder may e.g., inhibit or block the pro-apoptotic effect that is exerted by said at least one modified neurotrophin on motor neurons, and/or inhibit or block the neurite outgrowth stimulation and/or induction effect exerted by said at least one modified neurotrophin on sensory ganglia.

Preferably, a binder or specific binder of the invention does not bind to the non-nitrated pro-neurotrophin (i.e., the native pro-neurotrophin), from which the unmodified native mature neurotrophin derives. More preferably, a binder or specific binder of the invention does not bind to any non-nitrated pro-neurotrophin (i.e., to any native pro-neurotrophin).

A binder or specific binder of the invention may nevertheless bind to nitrated neurotrophin as well as to nitrated pro-neurotrophin.

Other binders or specific binders of the invention may bind to nitrated neurotrophin, without binding to nitrated pro-neurotrophin.

More preferably, a binder or specific binder of the invention does not bind to p75$^{NTR}$ and/or TrkA.

Said binder may e.g., bind to a nitrated epitope selected from QYFFETK (SEQ ID NO: 7), wherein the Tyr residue (Y) in position 2 of these epitopes bears at least one nitro group. This Tyr residue corresponds to Tyr52 of mouse NGF, or to Tyr52 of human NGF. This Tyr residue is highly conserved.

Said binder or specific binder of the invention may advantageously be an antibody, or a chemical that mimics the function of such an antibody.

Antibody and Antibody Mimics:

The antibody may be a polyclonal (e.g., a polyclonal serum) or a monoclonal antibody, including but not limited to fully assembled antibody, single chain antibody, Fab fragment, and chimeric antibody, humanized antibody.

The antibody of present invention may also be used in combination with other therapeutic agents such as proteins, antibodies, and/or with targeting molecules to specifically target a certain cell type, and/or to detection label, such as a radio-isotope to easily detect said antibody.

Means enabling to produce antibodies are known to the person of skilled in the art.

Animals can be immunized with a nitrated neurotrophin (or fragment or variant thereof), or an antigenic functional derivative thereof, according to a known method.

Appropriate animals notably comprise mammals, more particularly non-human mammals, such as rabbit.

For example, a mammal is injected intraperitoneally or subcutaneously with said nitrated neurotrophin (or fragment or variant thereof), or an antigenic functional derivative thereof.

Said nitrated neurotrophin (or fragment or variant thereof), or antigenic functional derivative thereof, may be diluted with, or suspended in an appropriate volume of PBS (Phosphate-Buffered Saline), physiological saline or the like.

An appropriate volume of a standard adjuvant can be mixed with the product, if necessary or desired. Illustrative standard adjuvants notably comprise Freund's (complete or incomplete) adjuvant, mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

It may be useful to conjugate said nitrated neurotrophin (or fragment or variant thereof) to a protein that is immunogenic in the species to be immunized, e.g., keyhole limpet hemocyanin (KLH), serum albumin, bovine thyroglobulin, or soybean trypsin inhibitor, by using a bifunctional or derivatizing agent, for example, maleimidobenzoyl sulfosuccinimide ester (conjugation through cysteine residues), N-hydroxysuccinimide (through lysine residues), glutaraldehyde, succinic anhydrid or $SOCl_2$.

The solution is administered to the animals several times, e.g., every 4 to 21 days. In addition, an appropriate carrier can also be used upon immunization with an immunogen.

Polyclonal antibodies are heterogeneous populations of antibody molecules, which can be derived from the sera of animals immunized with said at least one nitrated neurotrophin (or fragment or variant thereof), or an antigenic functional derivative thereof.

Monoclonal antibodies (mAb), which are homogeneous populations of antibodies to a particular antigen, may be obtained by any technique which provides for the production of antibody molecules by continuous cell lines in culture.

These include, but are not limited to the hybridoma technique of Kohler and Milstein (1975) Nature 256:495-497; and U.S. Pat. No. 4,376,110, the human B-cell hybridoma technique (Kosbor et al. (1983) Immunology Today 4:72; Cole et al. (1983) Proc. Natl. Acad. Sci. USA 80:2026-2030, and the EBV-hybridoma technique (Cole et al. (1985) Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing a mAb of this invention may be cultivated in vitro or in vivo.

Production of mAb of the invention notably comprises the collection of immunocytes, such as splenocytes, from an immunized animal, and the fusion of these immunocytes to a fusion partner.

As a partner cell to be fused with the above immunocyte, a mammalian myeloma cell can be used. Examples of a cell line of a myeloma cell that is preferably used herein include various known cell lines, such as the murine myeloma cell line SP2/0-Ag14, or a fused mouse myeloma/non-malignant B-lymphocyte cell line, such as the ATCC HB8464 cell line.

Cell fusion of the above immunocytes with myeloma cells can be basically performed according to a known method, for example, the method of Kohler and Milstein et al (Kohler. G. and Milstein, C., Methods Enzymol. (1981) 73, 3-46).

More specifically, the above cell fusion is performed in a standard nutrition culture solution in the presence of, for example, a cell-fusion accelerator. As a cell-fusion accelerator, for example, polyethylene glycol (PEG), hemagglutinating virus of Japan (HVJ) or the like is used. If desired, an adjuvant such as dimethylsulfoxide can also be used by addition to further enhance fusion efficiency.

Any ratio of immunocytes to myeloma cells may be set for use herein. For example, it is preferable that the number of immunocytes be 1 to 10 times greater than that of myeloma cells. As a culture solution to be used for the above cell fusion, for example, a RPM11640 culture solution or a MEM culture solution which is appropriate for the growth of the above myeloma cell line, or other standard culture solutions that are used for this type of cell culture can be used. Moreover, a serum fluid such as fetal calf serum (FCS) can be used in combination therewith.

Cell fusion is performed by mixing sufficiently certain amounts of the above immunocytes and myeloma cells in the above culture solution, adding a PEG (e.g., with an average molecular weight of approximately 1000 to 6000) solution (a general concentration of 30 to 60% (w/v)) pre-heated at approximately 37° C., and then mixing the solution, so as to form target fused cells (hybridomas). Subsequently, an appropriate culture solution is added successively, and then a step of removing the supernatant by centrifugation is repeated, so that reagents for cell fusion or the like that is unfavorable for the growth of the hybridomas is removed.

The thus obtained hybridomas are selected by culturing the hybridomas in a standard selective culture solution such as a HAT culture solution (a culture solution containing hypoxanthine, aminopterin and thymidine). Culture in the above HAT culture solution is continued for a time period sufficient for the cells (unfused cells) other than the target hybridomas to die (normally, several days to several weeks). Subsequently, a standard limiting dilution method is conducted, so that screening for and monocloning of hybridomas that produce a target antibody are performed.

In addition to a method with which the above hybridomas are obtained by immunizing non-human animals with antigens, desired human antibodies having binding activity to said nitrated neurotrophin (or fragment or variant thereof) can also be obtained (see Japanese Patent Publication (Kokoku) No. 1-59878 B (1989)), by sensitizing in vitro human lymphocytes with said nitrated neurotrophin (or fragment or variant thereof), or a functional antigenic derivative thereof, and causing the sensitized lymphocytes to fuse with the human-derived myeloma cells having a permanent division potential.

The thus prepared hybridomas producing monoclonal antibodies can be passage-cultured in a standard culture solution, or can be stored for a long period in liquid nitrogen.

One example of a method employed to obtain monoclonal antibodies from the hybridomas involves culturing the hybridomas and obtaining monoclonal antibodies in the culture supernatant according to a standard method. Another method involves administering the hybridomas to mammals that are compatible with the hybridomas to cause them to proliferate, and obtaining monoclonal antibodies in the ascites. The former method is suitable to obtain antibodies of high purity. On the other hand, the latter method is suitable for the mass production of antibodies.

A monoclonal antibody that can be used in the present invention can be a recombinant monoclonal antibody that is prepared by cloning the antibody gene from the hybridoma, incorporating the gene into an appropriate vector, introducing the vector into a host, and then causing the host to produce the recombinant monoclonal antibodies by genetic engineering techniques (e.g., see Vandamme, A. M. et al., Eur. J. Biochem. (1990) 192, 767-775, 1990).

In addition to the above host cell, a transgenic animal or plant can also be used to produce a recombinant antibody.

In addition to the above antibody, artificially altered gene recombinant antibodies such as chimeric antibodies or humanized antibodies can be used for, for example, lowering heteroantigenicity against a human. These altered antibodies can be produced using a known method.

Chimeric antibodies can e.g., be obtained by ligating the DNA encoding the antibody V-region to a DNA encoding a human antibody C-region, incorporating the product into an expression vector, and then introducing the vector into a host to cause the host to produce the antibodies. Using this known method, chimeric antibodies useful in the present invention can be obtained.

Humanized antibodies are also referred to as reshaped human antibodies, which are prepared by grafting an antibody CDR (complementarity determining region) of a mammal other than a human, such as a mouse, to the CDR of a human antibody. The general gene recombination technique thereof is also known (see European Patent Application Publication EP 125023 and WO 96/02576, or any one of their US counterparts, such as e.g., U.S. Pat. No. 6,068,040).

An antibody used in the present invention is not limited to the whole molecule, and may be a fragment of the antibody or the modified product thereof, as long as it still binds to at least one nitrated neurotrophin (or fragment or variant thereof) and has retained the capacity of inhibiting and/or blocking the apoptotic effect exerted by said at least one nitrated neurotrophin (or fragment or variant thereof) on motor neurons, and/or the capacity of inhibiting and/or blocking the stimulation and/or induction effect exerted by said at least one nitrated neurotrophin (or fragment or variant thereof) on sensory ganglia.

Multivalent, preferably bivalent, antibody and a monovalent antibody are included. Examples of the fragment of an antibody include Fab, F(ab')2, Fv, Fab/c having one Fab and a complete Fc, and a single chain Fv (scFv) wherein the Fv of the H-chain or the L-chain is ligated with an appropriate linker. Specifically, an antibody fragment is synthesized by treating the antibody with an enzyme such as papain or pepsin, or genes encoding these antibody fragments are constructed, the genes are introduced into expression vectors, and the genes are then expressed by appropriate host cells (see e.g., Rousseaux, J. et al., Methods in Enzymology (1989) 121, 663-669, and Bird, R. E. et al., TIBTECH (1991) 9, 132-137).

scFv is obtained by linking the H-chain V-region and the L-chain V-region of antibodies. In the scFv, the H-chain V-region and the L-chain V-region are linked via a linker, or preferably a peptide linker (Huston, J. S. et al., Proc. Natl. Acad. Sci. U.S.A. (1988) 85, 5879-5883). The H-chain V-region and the L-chain V-region in scFv may be derived from any of those described as antibodies in this specification. As a peptide linker to link the V-regions, for example, any single-stranded peptide comprising 12 to 19 amino acid residues is used.

A DNA encoding scFv can be obtained as follows. Amplification is performed by the PCR method using as templates the entire or DNA portions encoding desired amino acid sequences (of a DNA encoding the H-chain or the H-chain V-region of the above antibody, and a DNA encoding the L-chain or the L-chain V-region), and using a primer pair that specifies both ends. Amplification is then further performed by a combined use of a DNA encoding a peptide linker portion and a primer pair that specifies to cause both ends to ligate respectively to the H-chain and L-chain.

Furthermore, once a DNA encoding scFv is prepared, expression vectors containing the DNAs, and hosts transformed with the expression vectors, can be obtained according to the standard method. In addition, by the use of the host, scFv can be obtained according to the standard method.

These antibody fragments can be produced using hosts by obtaining the genes thereof in a manner similar to the above method, and then causing the expression of the genes. The "antibody" in the present invention also encompasses these antibody fragments.

While transgenic mammalian cells (e.g., Chinese hamster ovary cells) grown in culture are the industry standard for producing full length mAb, mammalian cells may be less suited for the production of antibody fragments such as Fab or scFv, and prokaryotic expression systems (e.g., E. coli) or other eukaryotic expression systems, such as yeast or plant cells, may preferably be used Furthermore, the antibody used in the present invention may be a bispecific antibody, which can also be prepared by genetic engineering techniques.

The antibodies expressed and produced as described above can be isolated from the cells or host animals, and purified to a uniform level. Isolation and purification of the antibodies to be used in the present invention can be performed using affinity columns. An example of a column using a protein A column is a Hyper D, POROS, Sepharose F. F. (Pharmacia). Other standard isolation and purification methods that are employed for proteins may be used, and there is no limitation regarding their use. For example, a chromatography column other than the above affinity column, a filter, ultrafiltration, a method of salting out, dialyses and the like may be appropriately selected and combined for use, so that antibodies can be isolated and purified (Antibodies A Laboratory Manual. Ed Harlow, David Lane, Cold Spring Harbor Laboratory, 1988).

Chemicals that mimic the function(s) of an antibody can be produced.

There are several approaches to the structure and manufacture of chemicals that mimic the function(s) of an antibody of the invention.

One approach utilizes an alternative protein framework, such as cytochrome b562, or structures comprising ribonucleic acids (RNA) (Hsieh-Wilson et al. 1996, Acc. Chem. Res. 29:164-170).

Unnatural oligomers, such as benzodiazepines, beta-turn mimics, protease inhibitors and purine derivatives have also been tested for their ability to function as antibody mimics.

Unnatural biopolymers, such as oligocarbamates, oligoureas and oligosulfones, have been proposed as antibody mimics.

Molecules with some of the recognition properties of antibodies have been created by joining various substituents to scaffolds such as xanthese or cubane, or a calixarene unit. These molecules have multiple peptide loops as the recognition site, but built around the relatively rigid organic framework formed by the scaffold.

The invention more particularly relates to those antibody mimics that have a capacity of inhibiting and/or blocking the apoptotic effect exerted by a nitrated neurotrophin (or fragment or variant thereof) on motor neurons, and/or of inhibiting and/or blocking the stimulation and/or induction effect exerted by a nitrated neurotrophin (or fragment or variant thereof) on sensory ganglia.

Biological Systems to Screen for Competitors of a Modified Neurotrophin of the Invention:

There are also several approaches to the structure and manufacture of biological systems that can be used to screen molecules that compete with a modified neurotrophin of the invention (or of a conservative fragment or variant thereof). One of the preferred systems is a ribosomal display system. A ribosomal display system comprises at least one ribosome, at least one protein and at least one mRNA encoding this protein. Advantageous ribosomal display systems have been described in Hanes and Plückthun 1997, Proc. Natl. Acad. Sci. USA, vol. 94, pages 4937-4942. Such ribosomal display systems can be applied to an antibody of the invention, more particularly to a specific antibody of the invention, advantageously to a scFv of the invention, more particularly to a specific scFv of the invention.

The invention thus also relates to a ribosomal display system, which consists of at least one ribosome, to which at least one scFv of the invention (more particularly at least one specific scFv of the invention), as well as at least one mRNA encoding such a scFv, are attached.

Such biological systems, and more particularly such ribosomal display systems, can advantageously be used to screen for compounds that bind to such a biological system, and preferably for compounds that compete with at least one modified neurotrophin of the invention (or a conservative fragment or a conservative variant) for binding to said biological systems.

Such compounds are thereby identified and isolated.

Preferred compounds are those which bind to a ribosomal display system of the invention (which preferably comprises at least one ribosome, at least one specific scFv of the invention, and at least one mRNA encoding this scFv), without cross-reacting with (i.e., without binding to) another ribosomal display system, wherein said other ribosomal display system also comprises at least one ribosome, at least one antibody (e.g., a scFv), and at least one mRNA encoding this antibody, but wherein said antibody (said scFv) binds to at least one neurotrophin, without binding to any of the modified neurotrophins that could be obtained from this at least one neutrophin.

The invention more particularly relates to those compounds that have a capacity of modulating, preferably of inhibiting and/or blocking, the apoptotic effect exerted by a nitrated neurotrophin (or fragment or variant thereof) on motor neurons, and/or of modulating, preferably of inhibiting and/or blocking, the stimulation and/or induction effect exerted by a nitrated neurotrophin (or fragment or variant thereof) on sensory ganglia.

Such compounds may exert their modulation activity, preferably their inhibitory or blocking activity, by competing with endogenous nitrated neurotrophins for binding to their endogenous target(s), such as e.g., TrkA, $p75^{NTR}$, or other receptors or co-receptors, such as sortilin.

Therapeutic and Diagnostic Applications:

A modified neurotrophin of the invention (or a conservative fragment or variant thereof) has the capacity of inducing and/or stimulating the apoptosis of motor neurons, and/or the neurite outgrowth from sensory ganglia.

Non-conservative fragments of a modified neurotrophin can be produced by the person of average skilled in the art, e.g., by peptide or polypeptide synthesis.

Non-conservative variants of a modified neurotrophin, or of a modified neurotrophin fragment, which derive from said modified neurotrophin, or modified neurotrophin fragment, by at least one amino acid substitution and/or deletion and/or addition, can also be produced by the person of average skilled in the art, e.g., by peptide or polypeptide synthesis.

Such non-conservative fragments or variants have lost the capacity of inducing and/or stimulating motor neuron apoptosis and/or neurite outgrowth, or at the very least do not show a detectable capacity for such an induction and/or stimulation when injected into a mammal.

Such a non-conservative fragment or variant may be antigenic on and of its own, or can be associated with at least one other compound (such as an adjuvant, added in association, or by conjugation), to become antigenic, or to have an increased antigenicity.

Such a non-conservative fragment or variant may thus be used as an agent for active immunization. When administered to a mammal, such a human being, in need thereof, it can induce and/or stimulate an immune response, and more particularly an antibody response, whereby antibodies binding to at least one modified neurotrophin of the invention (or conservative fragment or variant thereof) are being produced by said mammal.

Preferred non-conservative fragments or variants are those which can induce and/or stimulate an antibody response, whereby antibodies, which bind to at least one modified neurotrophin of the invention (or conservative fragment or variant thereof) but which do not bind to the non-modified (healthy) native neurotrophin, are being produced by said mammal.

Such a non-conservative fragment or variant is useful as an antigen to induce an immune antibody response for the therapy and/or palliation and/or prevention of the apoptosis of motor neurons and/or the outgrowth of neurite. Hence, such a modified neurotrophin of the invention (or a conservative fragment or variant thereof) is useful as an agent for the treatment and/or palliation and/or prevention of pain, and/or as an agent for the treatment and/or palliation and/or prevention of a neurodegenerative disease or condition.

Compounds, such as those that can be identified and isolated by screening with a ribosomal display system of the invention, can compete with the activities of a modified neurotrophin of the invention (or a conservative fragment or variant thereof), thereby blocking and/or inhibiting the apoptosis of motor neurons, and/or the neurite outgrowth from sensory ganglia.

When administered to a mammal, such a human being, in need thereof, such a compound is useful to block and/or inhibit the apoptosis of motor neurons, and/or the neurite outgrowth from sensory ganglia.

A binder of the invention, such an antibody of the invention, and more particularly a specific antibody of the invention, binds to a modified neurotrophin of the invention (or a conservative fragment or variant thereof).

Such a binder is useful as an agent for passive immunization. When administered to a mammal, such a human being, in need thereof, such a binder will bind to said modified neurotrophin of the invention (or a conservative fragment or variant thereof), thereby blocking and/or inhibiting the apoptosis of motor neurons, and/or the neurite outgrowth from sensory ganglia.

Such a binder is useful as agent to block and/or inhibit the apoptosis of motor neurons, and/or the neurite outgrowth from sensory ganglia.

Such a binder is useful as an agent for passive immunization therapy and/or palliation and/or prevention of the apoptosis of motor neurons and/or the outgrowth of neurite. Hence, such a binder is useful as an agent for the treatment and/or palliation and/or prevention of pain, and/or as an agent for the treatment and/or palliation and/or prevention of a neurodegenerative disease or condition.

The invention also relates to any composition, which comprises:
  at least one element selected from the group comprising the non-conservative fragments and the non-conservative variants of the invention, or which comprises
  at least one of said competing compounds, or which comprises
  at least one element selected from the group comprising the binders of the invention (more particularly the specific binders of the invention, still more particularly the antibodies, the chemical mimics, and the biological mimics of the invention).

Such compositions may further comprise at least one element selected from excipient, diluent, buffer, pharmaceutical vehicle, physiologically acceptable vehicle, adjuvants.

The invention relates to such pharmaceutical compositions, immunogenic compositions, immunological compositions, drugs, or vaccines.

When used as antigen for active immunization, at least one element selected from the group comprising the non-conservative fragments and the non-conservative variants of the invention, or an antigenically functional equivalent thereof, may be administered to a mammal, preferably a human, via a variety of routes.

When used for passive immunization, a binder of the invention of the present invention (and more particularly a specific binder, e.g. a specific mAb), or an antigenically functional equivalent thereof, may be administered to a mammal, preferably a human, via a variety of routes.

These routes notably include orally, parenterally, intraperitoneally, intravenously, intraarterially, topically, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The antibody may also be delivered to the host locally (e.g., via stents or catheters) and/or in a timed-release manner.

A binder of the invention (e.g., an Ab), and more particularly a specific binder of the invention (e.g., a specific mAb), is also useful for determining the presence, or the excessive presence, of a modified neurotrophin of the invention (or a conservative fragment or variant thereof) in an animal, such as a mammal (e.g. a human being), and more particularly in a sample collected from such an animal.

The excessive presence of such a modified neurotrophin of the invention (or a conservative fragment or variant thereof) is indicative of the existence or of a risk to develop a neurodegenerative disease or condition, or a pain condition.

A binder of the invention (e.g., an Ab), and more particularly a specific binder of the invention (e.g., a specific mAb), is thus also useful for the diagnosis of the existence, or the risk to develop, a condition or disease involving motor neuron apoptosis and/or neurite outgrowth.

Diseases or conditions wherein it is useful to block and/or inhibit the apoptosis of motor neurons notably comprise neurodegenerative conditions or diseases, ALS (Amyotrophic Lateral Sclerosis), Alzheimer's disease, Huntington disease's, Multiple Sclerosis, any disease or condition involving a memory deficit and/or a concentration disorder, as well as neuroinflammatory conditions or diseases.

Diseases or conditions wherein it is useful to block and/or inhibit the neurite outgrowth from sensory ganglia notably comprise pain state or conditions or feelings, and more particularly:
  neuropathic pain (more particularly, migraine, chronic migraine, probable analgesic-abuse headache PAAH, primary fibromyalgia syndrome PFMS, nerve-injury induced neuropathic pain, sciatic nerve lesions, chronic constriction injury),
  articular pain (more particularly, osteoarthritic conditions, osteoarthrosis, osteoarthritis),
  inflammatory pain,
  cancer pain.

The invention also relates to any composition, which comprises at least one element selected from the group comprising the modified neurotrophins of the invention, the conservative fragments thereof, and the conservative variants of such a modified neurotrophin or of such a conservative fragment.

Such compositions may further comprise at least one element selected from excipient, diluent, buffer, pharmaceutical vehicle, physiologically acceptable vehicle, adjuvants.

The invention relates to such pharmaceutical compositions, immunogenic compositions, immunological compositions, drugs, or vaccines.

Such compositions are useful to induce and/or stimulate motor neuron apoptosis and/or neurite outgrowth.

They are thus useful for the prevention and/or treatment and/or palliation of diseases or conditions where the stimulation and/or induction of motor neuron apoptosis and/or of neurite outgrowth is desired, preferably for the prevention and/or treatment and/or palliation of diseases or conditions where the stimulation and/or induction of neurite outgrowth is desired, such as diseases, conditions or trauma that result in neuropathy and nerve injury, including stroke, spinal cord injuries, and neurodegenerative illnesses.

The present application also relates to a method for the treatment and/or palliation and/or prevention of such diseases or conditions, which comprises administering to a mammal in need thereof an effective amount of an antibody, antibody fragment, or scFv,
wherein said antibody, antibody fragment, or scFv binds to at least one nitro-neurotrophin, wherein said at least one nitro-neurotrophin comprises at least one nitro group on at least one residue selected from its Tyr and Trp residues,
without cross-reacting with a non-nitrated neurotrophin.

The present application also relates to a method for determining whether there is an abnormal post-translational modification of a neurotrophin structure, in a sample suspected of containing such a neurotrophin structure, which comprises determining whether a binder of the invention, such as an antibody of the invention, more particularly a specific binder of the invention, such as a specific antibody of the invention, binds to a target contained in said sample, whereby such a binding is indicative of the presence in said sample of a neurotrophin structure that has undergone abnormal post-translational modification.

Said abnormal post-translational modification notably comprises nitration of said neurotrophin structure, as above explained and as below illustrated.

The present application also relates to a method and a kit for the diagnosis of a disease or condition involving motor neuron apoptosis and/or neurite outgrowth, such as the diseases and conditions that are above-listed.

The kit of the invention comprises at least one binder of the invention, such as at least one antibody of the invention, more particularly at least one specific binder of the invention, such as at least one specific antibody of the invention.

The diagnosis method of the invention comprises determining whether a binder of the invention, such as an antibody of the invention, more particularly a specific binder of the invention, such as a specific antibody of the invention, binds to a target (i.e., a ligand) contained in the mammal that is subjected to said diagnosis, preferably in a representative sample collected from such a mammal (i.e., a sample that can be suspected of containing neurotrophin structures), whereby such a binding is indicative of the fact that said mammal has said disease or condition, or is at high risk of developing such a disease or condition.

In the present application the term "diagnosis" thus encompasses the determination of an existing disease or condition, as well as the prediction of its development, or at the very least the evaluation of the propensity of the subject to develop such a disease or condition.

Method of Screening:

The invention also relates to a method of screening for compounds that are capable of inhibiting and/or blocking the apoptotic activity that a modified neurotrophin of the invention (or a conservative fragment or variant thereof) may have on motor neurons, and/or the neurite outgrowth effect that a modified neurotrophin of the invention (or a conservative fragment or variant thereof) may have on sensory ganglia.

Candidate compounds can be screened for their capacity of binding to at least one binder of the invention (e.g., at least one antibody of the invention), more particularly to at least one specific binder of the invention (e.g., at least one specific antibody of the invention, such as a specific mAb of the invention), or to at least one ribosomal display system of the invention, whereby such a binding capacity is indicative of a potential to inhibit and/or block said apoptotic activity and/or said neurite outgrowth effect.

Preferred compounds are those compounds, which do not bind to a mAb that is specific of unmodified native neurotrophin (i.e., a mAb, which binds to unmodified native neurotrophin, without binding to the modified neurotrophin that derives therefrom).

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

Each of the relevant disclosures of all references cited herein is specifically incorporated by reference. The following examples are offered by way of illustration, and not by way of limitation.

EXAMPLES

Abstract

Nerve growth factor (NGF) overexpression and increased production of peroxynitrite occur in several neurodegenerative diseases. We investigated whether NGF could undergo post-translational oxidative or nitrative modification that would modulate its biological activity. Compared to native NGF, peroxynitrite-treated NGF showed the exceptional ability to induce $p75^{NTR}$-dependent motor neuron apoptosis at physiologically relevant concentrations. While native NGF requires an external source of nitric oxide (NO) to induce motor neuron death, peroxynitrite-treated NGF induced motor neuron apoptosis in the absence of exogenous NO. Nevertheless, NO potentiated the apoptotic activity of peroxynitrite-modified NGF. Blocking antibodies to $p75^{NTR}$ or downregulation of $p75^{NTR}$ expression by antisense treatment prevented motor neuron apoptosis induced by peroxynitrite-treated NGF. We investigated what oxidative modifications were inducing this toxic gain of function and found peroxynitrite induced tyrosine nitration in a dose dependent manner. Moreover, peroxynitrite triggered the formation of stable high molecular weight oligomers of NGF, although no evidence of 3,3'-dityrosine cross-linking was observed. Preventing tyrosine nitration by urate abolished the effect of peroxynitrite on NGF apoptotic activity. These results indicate that the oxidation of NGF by peroxynitrite enhances NGF apoptotic activity through $p75^{NTR}$ 10,000 fold. To our knowledge, this is the first known post-translational modification that transforms a neurotrophin into an apoptotic agent.

Introduction

We investigated whether NGF could undergo post-translational oxidative or nitrative modification, altering its functional activity. We report that oxidation of NGF by peroxynitrite in vitro causes nitration and induces the formation of high molecular weight oligomers. Moreover, these oxidative modifications confer the exceptional ability to induce $p75^{NTR}$-dependent motor neuron apoptosis at physiological relevant concentrations. Our data show that oxidative stress by peroxynitrite can critically modulate neurotrophin activity.

Materials and Methods

Peroxynitrite Treatment.

Peroxynitrite is notably available from Upstate (e.g., Upstate USA, Charlottesville, Va. 22903, USA). Peroxynitrite concentration was determined spectrophotometrically at 302 nm ($\epsilon$=1,670 $M^{-1}$ $cm^{-1}$). Diluted stock solutions were freshly prepared in 0.01 M NaOH. The reactions of NGF (Harlan; Indianapolis, USA) with different concentrations of peroxynitrite (0.25 mM to 2 mM) was performed at a protein concentration of 0.2 mg/mL to 1.0 mg/mL obtaining similar results. The reaction was performed in 50 mM sodium phosphate buffer, pH 7.4, containing 20 mM sodium bicarbonate. NGF was subjected to 10 bolus addition of peroxynitrite (1 μL each) to reach the desired final concentration of peroxynitrite. One bolus of peroxynitrite stock solution was rapidly added on the top of the test tube and mixed by vortexing for 3 sec. The procedure was repeated 10 times. To exclude a potential non-specific effect of peroxynitrite treatment because of pH changes or contaminants, control experiments were performed using diluted NaOH or decomposed peroxynitrite (reverse order addition, ROA). Treatment of bovine serum albumin (Sigma), FGF-1 (Sigma) and FGF-2 (R&D Systems) with peroxynitrite was performed as described above at a concentration of 0.2 mg/mL.

NGF Nitration by Tetranitromethane.

The reaction of NGF (Harlan) with a 40-fold molar excess of tetranitromethane (Sigma) was performed at a protein concentration of 1 mg/mL in 0.1 M Tris-HCl buffer, pH 8.0 for 40 min. The reaction was finished by passing the reaction mixture through a Sephadex G-25 column equilibrated with and developed in 0.05 M ammonium bicarbonate, pH 8.0.

Electrophoretic Analysis and Western Blot.

SDS-PAGE was performed in 15% polyacrylamide minigels under reducing conditions. Samples were boiled for 5 min in LaemLi buffer before running. Proteins were visualized by Coomassie Blue or Silver staining. For Western Blot analysis proteins were transferred to nitrocellulose membranes (Hybond-ECL, Amersham). Membranes were blocked for 2 h in blocking solution (5% BSA, 0.1% Tween 20 in Tris-buffered saline (TBS), pH 7.4) followed by an overnight incubation with the primary antibody diluted in blocking solution. After washing with 0.1% Tween in TBS the membrane was incubated with peroxidase-conjugated goat anti-rabbit antibody (1:4000; Bio-Rad) for 1 h, and then washed and developed using the ECL chemiluminescent detection system (Amersham). Primary antibodies used were anti-NGF-β polyclonal antibody (1:3000; Chemicon) and polyclonal antibody to nitrotyrosine (1:3500; Upstate).

Size Exclusion Chromatography Coupled to Multi-Angle Light Scattering.

Samples of NGF treated with peroxynitrite (1 mM) or decomposed peroxynitrite at a concentration of 0.5 mg/mL were injected onto a Biosuite 125 HPLC size exclusion column (Waters) connected in line with a DAWN-EOS Multi-Angle Light Scattering Detector and an OptilabRex refractometer (Wyatt Tech. Corp.). The HPLC column was equilibrated with and developed in 50 mM sodium phosphate, 50 mM sodium sulphate buffer, pH 7.2. The light scattering unit was calibrated following manufacturer's instructions. A value of 0.185 mL/g was assumed for the do/dc of the protein. The detector responses were normalized by measuring the signal for monomeric bovine serum albumin. The temperature of the light scattering unit and of the refractometer were maintained at 25° C. The column and all external connections were at ambient temperature (approximately 25° C.). The flow rate was maintained at 0.5 mL/minute throughout the experiments.

Mass Spectrometry Studies.

Samples of native NGF or NGF treated with tetranitromethane or peroxynitrite (1 mM) at a concentration of 1 mg/mL, were separated by reverse-phase high pressured liquid chromatography (HPLC). The stationary phase was a $C_{18}$ reverse phase Supelco column (15 cm×4.6 mm, 5 µM). The mobile phase was $H_2O/CH_3CN$ and 0.1% trifluoroacetic acid. A linear gradient increasing 5% to 60% organic over 55 minutes was used to achieve seperation. Samples were collected by a fraction collector, concentrated in vacuo, and resuspended to be divided for mass spectrometric analysis for total molecular weight changes or analysis of the tryptic digest. To find total changes in molecular weight, collected fractions were resuspended in 30% acetonitrile with 0.1% formic and then directly injected into a Waters/micromass LCT Classic electrospray time of flight mass spectrometer. The mobile phase was 30% acetonitrile, 0.1% formic acid with 5 µL/min flow rate. The capillary voltage was 3.018 kV, the source temperature was 80° C., and sample cone voltage was 45 V. Tryptic digests were performed by resuspension in a 0.1% RapiGest™ solution in 50 mM ammonium bicarbonate buffer and was carried out according to RapiGest™ SF Powder protocol. Briefly, samples were reduced with DTT and blocked with IAA before incubating with trypsin (1:50, µg trypsin: µg protein) overnight at 37° C. TFA was added to digested protein samples to a final concentration of 0.5% and samples were centrifuged at 13000 rpm for ten minutes. A NanoAcquity Waters HPLC system was used to inject samples onto the Waters Q-tof Ultima Global Mass spectrometer. Samples were loaded at 2 µL/min onto a Jupiter $C_{18}$ trap and then washed for six minutes with water and 0.1% formic acid at 1 µL/min. Samples were eluted using a gradient (0.26 µL/min) which began at 2% acetonitrile, 0.1% formic acid and increased organic at ~2%/min over 45 minutes. Samples were separated over Waters BEH $C_{18}$ material in a New Objective pico-frit, 10 cm column and then injected using a Waters Nano Lockspray source with electrospray capillary voltage at 3.5 kV and source voltage, 70 kV. Data dependent tandem mass spectrometry was performed with collision energy that was dependent upon the m/z of the parent ion. The $MS^2$ spectra were searched using Mascot MS/MS ion search engine and the peptides reported received scores of identity or above.

Purified Motor Neuron Cultures.

Media and sera were purchased from Gibco-Invitrogen. Motor neuron cultures were prepared from embryonic day 15 (E15) rat spinal cord by a combination of metrizamide gradient centrifugation and immunopanning with a monoclonal antibody directed against rat p $75^{NTR}$ (mouse mAb Ig192) as previously described [44]. Motor neurons were plated at a density of 350 cells/cm² on 4 well multidishes (Nunclon) precoated with polyornithine-laminin. Cultures were maintained in Neurobasal™ medium supplemented with 2% horse serum, 25 mM L-glutamate, 25 µM 2-mercaptoethanol, 0.5 mM L-glutamine, and 2% B-27 supplement (Gibco-Invitrogen). Motor neuron survival was maintained by the addition of GDNF (1 ng/mL; Sigma) to the culture media. Motor neuron death induced by trophic factor deprivation (NONE, without GDNF) was determined in all experiments as a control, and never was greater than 50%. Treatments with the different reagents were performed 3 hours after motor neuron plating. Motor neuron survival was assessed after 48 hours by direct counting of all cells displaying intact neurites longer than 4-cell bodies in diameter, in a prefixed area of the dish.

Antisense Treatment.

Treatment with antisense oligonucleotides to down-regulate $p75^{NTR}$ expression was performed as described previously [45]. Briefly, HPLC-purified phosphorothioate antisense and missense oligonucleotides (5 µM; Integrated DNA Technologies) were added to the cell suspension of purified motor neurons and repeatedly pipetted before seeding. The oligonucleotides were present the whole time of culture. To determine the efficiency of uptake, cultures were incubated with $p75^{NTR}$ antisense oligonucleotides with a 5' 56-FAM fluorescent label. Cells were transferred to the heated stage (37° C.) of a Zeiss LSM510 confocal microscope with constant 5% $CO_2$. Fluorescence was imaged with a 63× oil immersion objective. Uptake efficiency was >96% in all experiments. Sequences used were: $p75^{NTR}$ antisense, 5'-ACCTGCCCTCCTCATTGCA-3' (SEQ ID NO: 5) and p $75^{NTR}$ missense, 5'-CTCCCACTCGTCATTCGAC-3' (SEQ ID NO: 6) [45]. The antisense sequence used has been shown to be effective at inhibiting $p75^{NTR}$-dependent motor neuron death in vivo [20].

Statistics.

Each experiment was repeated at least three times and data are reported as mean±SD. Comparison of the means was performed by one-way analysis of variance. Pairwise contrast between means utilized the Student-Newman-Keuls test and differences were declared statistically significant if p<0.05. All statistics computations were performed using the SigmaStat Software (Jandel Scientific).

Secretion of Nitro-NGF by Stimulated Astrocytes.

Conditioned media (concentrated 40× by ultra-filtration) from resting or stimulated astrocytes (FGF1, 10 ng/mL; and LPS, 5 microg/mL) were analysed by western blotting using a specific anti-nitro-NGF antibody. Standard NGF (50 ng, Harlan) or nitro-NGF (50 ng) were loaded in the first two lanes. The specific anti-nitro-NGF antibody that has been used is a polyclonal antibody, which has been obtained by immunization of rabbits against the nitro-NGF that is obtained by nitration of the commercially-available mouse NGF by peroxynitrite and by isolation the nitro-NGF species that are thereby produced. The specific anti-nitro-NGF antibody has been selected as binding to nitro-NGF without cross-reacting with the non-nitrated standard NGF.

Peroxynitrite Increases the Neurite Outgrowth Promoting Activity of NGF.

Dorsal root ganglia explants from E15 rat embryos (that express both TrkA and $p75^{NTR}$) were cultured in Neurobasal media in the absence of trophic factors (NONE) or in the presence of NGF (100 ng/mL), NGF treated with peroxynitrite (100 ng/mL; nitroNGF-P) or NGF treated with tetranitromethane (nitroNGF-TNM). After 24 hours cultures were fixed with 4% paraformaldehyde and processed for immunofluorescence against GAP-43. Note that ganglia treated with nitroNGF exhibit increased neurite growth compared to those treated with NGF.

Results

Oxidation by Peroxynitrite Enhances NGF Apoptotic Activity

In cultures maintained with GDNF (1 ng/mL), motor neurons expressing $p75^{NTR}$ are not sensitive to NGF. However, peroxynitrite-treated NGF induced motor neuron death at concentrations as low as 1 ng/mL (FIG. 2A). NGF treated with decomposed peroxynitrite (ROA) did not affect motor neuron survival (FIG. 2A). Peroxynitrite treatment enhanced NGF apoptotic activity in a dose-dependent manner, reaching a plateau at concentrations higher than 0.5 mM peroxynitrite (FIG. 2B). As previously reported [25], in the presence of a steady state concentration of nitric oxide<50 nM, generated from the nitric oxide donor DETA-NONOate (10 µM), NGF-ROA significantly induced motor neuron loss at concentrations higher than 10 ng/mL (FIG. 2C). Moreover, in the presence of nitric oxide, peroxynitrite-modified NGF showed increased apoptotic activity, inducing a 33% of motor neuron loss at only 1 pg/mL (FIG. 2C). The addition of peroxynitrite treated-BSA, -FGF-1 or -FGF-2 to motor neuron cultures did not induce motor neuron death (FIG. 2D), suggesting a specific effect of peroxynitrite treated NGF.

Figure 3A:
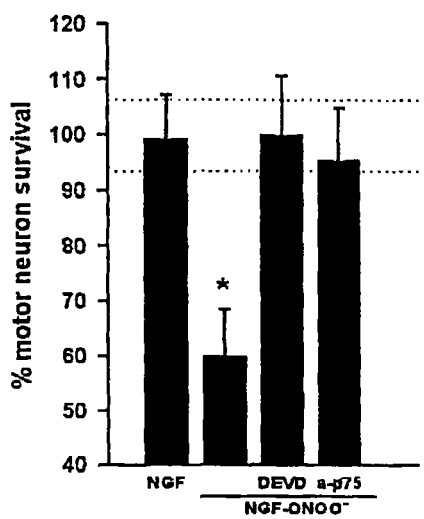
FIG. 3. The apoptosis mediated by peroxynitrite-treated NGF required $p75^{NTR}$. (A) Blocking antibodies to $p75^{NTR}$ (a-p75, 1:100, Chemicon #AB1554) and the general caspase inhibitor DEVD-fmk (10 μM) prevented motor neuron death induced by NGF (100 ng/mL) previously treated with peroxynitrite (1 mM; NGF-ONOO⁻). Antibodies to $p75^{NTR}$ were added once immediately after motor neuron plating while DEVD-fmk was added every 24 hours. Data are expressed as percentage of GDNF, mean±SD. Dashed lines represent the SD of GDNF. *Significantly different from GDNF (p≤0.05). (B) Antisense and missense oligonucleotides were added to purified motor neuron cultures at the time of plating. 24 h later, cultures were exposed to NGF-ONOO⁻ (100 ng/mL) or NGF (100 ng/mL) plus DETA-NONOate (10 μM) (NGF+ NO). Antisense oligonucleotides (black bars) completely blocked the loss of motor neurons induced by both treatments, whereas missense oligonucleotides (white bars) had no effect on neuronal survival. Data are expressed as percentage of the respective GDNF, mean±SD. *Significantly different from the respective GDNF (p≤0.05). (C) Motor neuron apoptosis induced by NGF-ONOO⁻ requires the endogenous production of peroxynitrite. Motor neuron cultures were treated with 1 mM peroxynitrite-treated NGF (100 ng/mL) in the presence L-NAME (1 mM) or MnTBAP (100 μM). Dashed lines represent the SD of GDNF. Data are expressed as percentage of GDNF, mean±SD. *Significantly different from GDNF (p≤0.05). Motor neuron survival was determined in all cases 48 h after treatment.
Figure 3B:
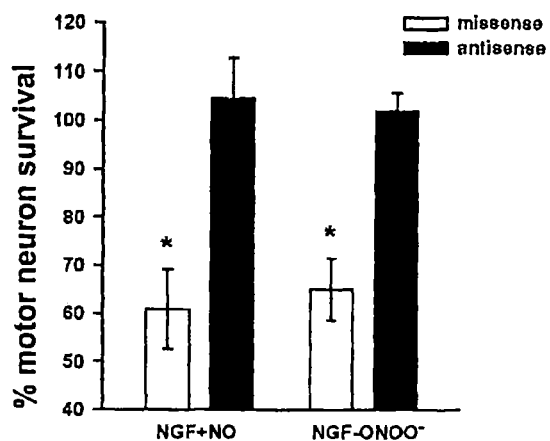
Figure 3C:
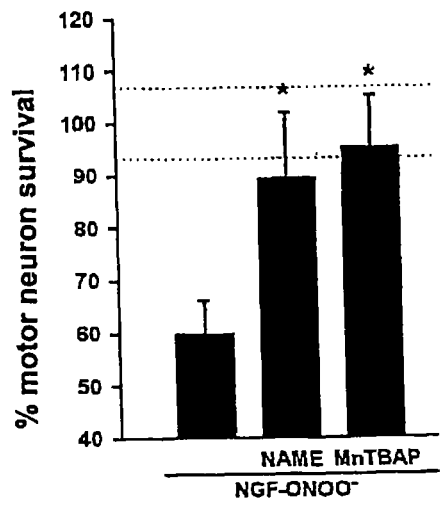

Motor neuron loss induced by peroxynitrite-treated NGF was blocked by the general caspase inhibitor DEVD-fmk (FIG. 3A), indicating the activation of an apoptotic mechanism. We have previously shown that NGF induces motor neuron apoptosis by signaling through $p75^{NTR}$ [25]. The apoptosis induced by peroxynitrite-treated NGF was also dependent on $p75^{NTR}$ activation since it was completely prevented by the addition of blocking antibodies to $p75^{NTR}$ (FIG. 3A) or the down-regulation of $p75^{NTR}$ expression by antisense treatment (FIG. 3B). As a control, antisense treatment also blocked motor neuron apoptosis induced by native NGF in the presence of nitric oxide (FIG. 3B). Motor neuron apoptosis induced by different apoptotic stimuli, including NGF, requires the endogenous production of peroxynitrite [25, 46-48]. Motor neuron loss induced by peroxynitrite-treated NGF was prevented by the general nitric oxide synthase (NOS) inhibitor, L-NAME (1 mM) or the SOD mimetic and peroxynitrite decomposition catalyst, MnTBAP (100 µM) (FIG. 3C), further confirming the execution of a similar apoptotic mechanism.

Peroxynitrite Induces NGF Oligomerization and Nitration

We then analyzed the modifications induced by peroxynitrite treatment on NGF. Exposure of NGF to successive bolus additions of peroxynitrite caused a dose dependent appearance of three high-molecular-weight species as revealed by SDS-PAGE. Staining intensity of native NGF progressively diminished with the increase in peroxynitrite concentration (FIG. 4A). Treatment of NGF with decomposed peroxynitrite (ROA) failed to induce this migration shift. The formation of NGF oligomers was confirmed in solution by HPLC size-exclusion chromatography coupled to real-time multi-angle light scattering (MALS) analysis (FIG. 4B). NGF treated with decomposed peroxynitrite (NGF-ROA) eluted from the size-exclusion column as a single peak with a mass corresponding to the dimer (33.0±1.2 KDa). In contrast, peroxynitrite-treated NGF eluted as three peaks, likely corresponding to dimer (33.2±0.6 KDa), tetramer (68.5±3.5 KDa) and octamer (125.0±10.0 KDa). Surprisingly, the peroxynitrite-treated NGF dimer eluted before the native dimer (NGF-ROA), reflecting the existence of conformational changes due to protein nitration.

Figure 6A:
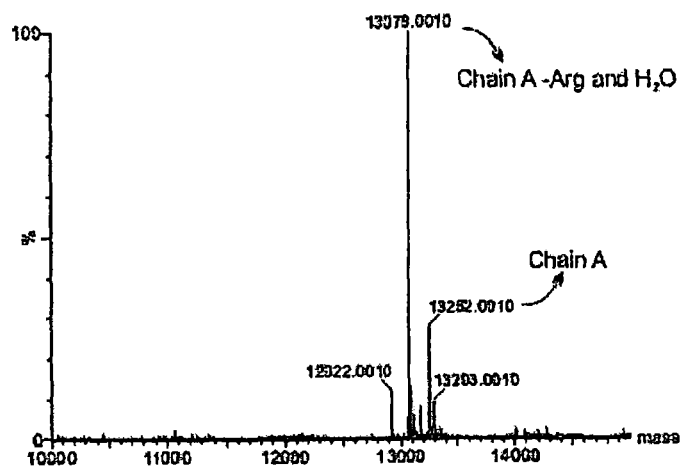
FIG. 6. Mass spectrometry of HPLC collected fractions. (A) Electrospray time-of-flight mass spectrometry of the eluent from native NGF at 36.3 minutes revealed a mass of 13,252 Da, corresponding to Chain A of NGF. Mass signal at 13,078 Da is consistent with the lack of the C-terminal arginine residue. (B) Mass spectrometry of the eluent at 38.6 minutes from peroxynitrite-treated NGF showed a 89 Da increase in Chain A mass (from 13,252 to 13,341 Da). The eluent at 39.9 minutes corresponded to Chain B and also showed an increase of 90 Da (from 12,357 to 12,449 Da).
Figure 6B:
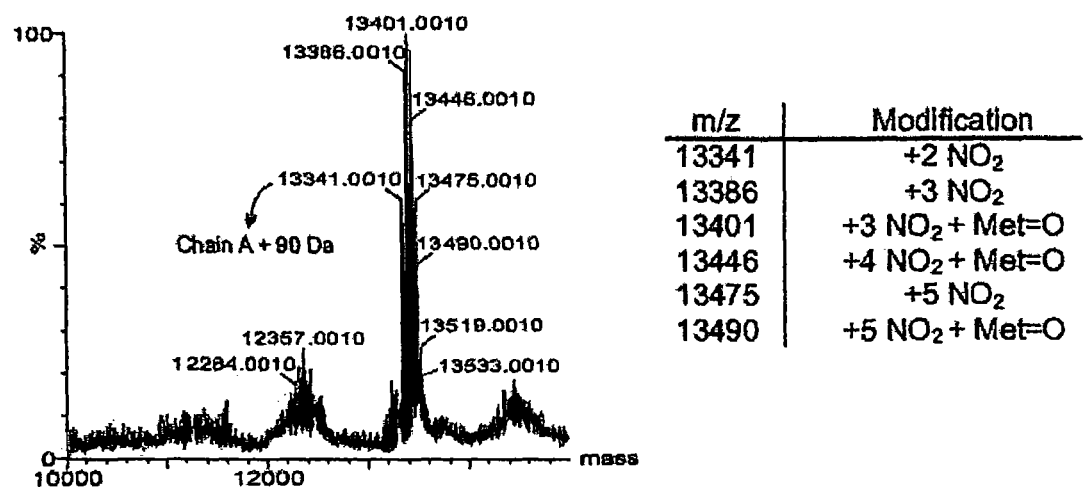

Peroxynitrite treatment also induced dose-dependent nitration of NGF, as revealed by reactivity with an anti-nitrotyrosine antibody (FIG. 4C). The specific sites of oxidative modifications were determined by mass spectrometry of purified oxidation products. Native NGF eluted as two peaks by reverse-phase HPLC, at 36.3 and 38.1 minutes (FIG. 5A), both identified as the NGF polypeptide chain by mass spectrometry. Chain B lacks the eight N terminals residues present in Chain A and is known to be formed due to limited proteolysis during NGF purification [40]. Oxidation of NGF by peroxynitrite resulted in the incomplete separation of several products as eluted by reverse-phase HPLC (FIG. 5B). Mass spectrometry of the peroxynitrite-treated fraction collected at 38.6 minutes revealed several species of increased molecular weight as compared to the mass spectrum of unmodified NGF (FIG. 6). As it has been previously described [40], some of the unmodified NGF chains lacked the C-terminal arginine residue (FIG. 6A). In peroxynitrite-treated NGF, the smallest mass shift was a ~90 Da increase of Chain A (from 13,252 Da to 13,341 Da), suggesting the addition of two nitro groups (45 Da each) (FIG. 6B). In addition, peroxynitrite treatment appeared to induce several additional modifications, suggesting up to five nitro groups and methionine oxidation. NGF contains three tryptophans and two tyrosines that might account for the five sites of nitration (Inserted Table of FIG. 6B). A similar pattern of modifications was observed for chain B of NGF.

Figure 7A:
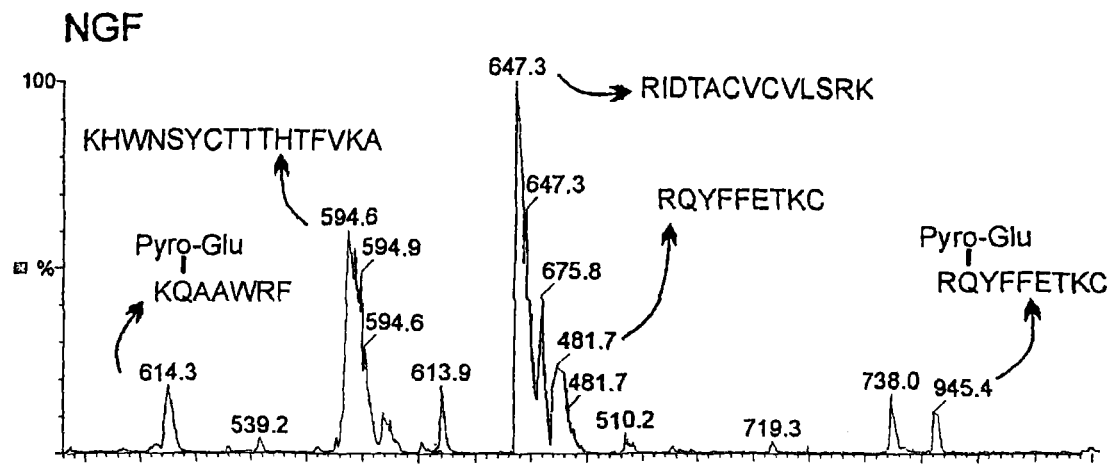
FIG. 7. Q-T of mass spectrometry of trypsin-digested HPLC collected fractions. HPLC purified samples were digested, analysed by Q-T of mass spectrometry and subsequent MS/MS ion searches were performed by Mascot. (A) Native untreated NGF eluent at 36.3 minutes, (B) eluent from peroxynitrite-treated NGF at 38.6 minutes showing modified peptides that indicate the nitration of Tyr52 and Trp99. Similar modifications were observed for the eluent at 39.9 minutes from peroxynitrite-treated NGF. Pyro-glutamic acid (Pyro-Glu) is a common modification of glutamine (Q) at the N-terminus of a peptide.
Figure 7B:
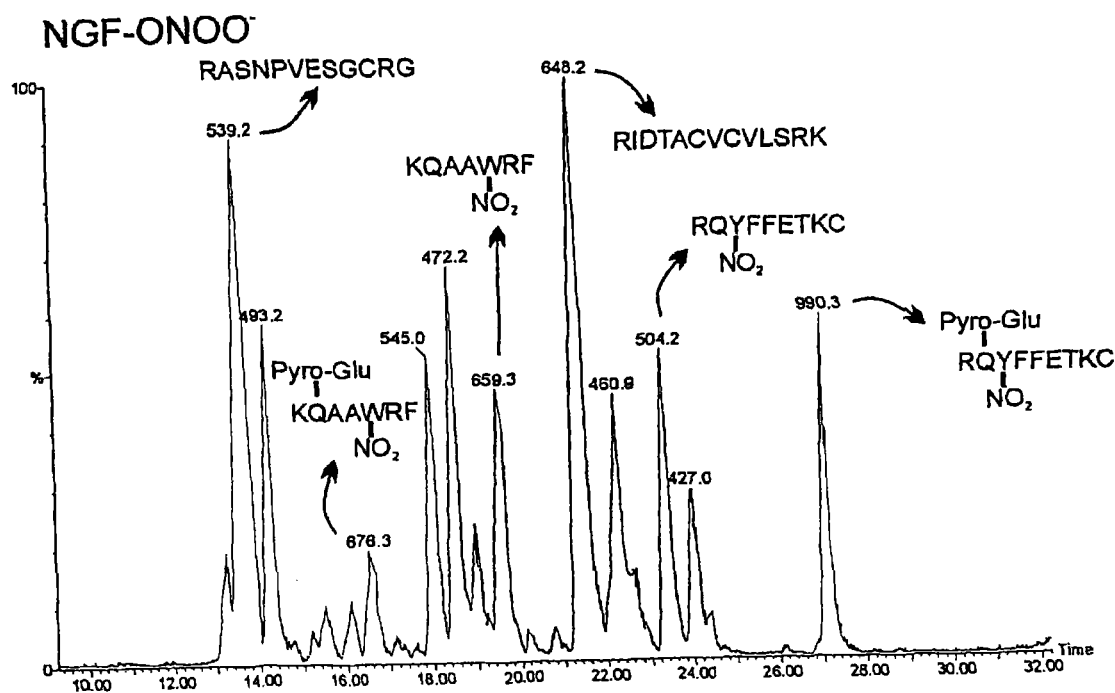

To identify the specific residue(s) undergoing oxidative modification, HPLC purified samples were digested and analysed by mass spectrometry. The comparison of untreated and peroxynitrite-treated NGF digests revealed the nitration of the two tyrosine residues, Tyr52 and Trp99 (FIG. 7), which may account for the detected total molecular weight change of 90 Da. Oxidation of NGF by peroxynitrite also resulted in loss of tryptophan fluorescence, supporting the nitration of tryptophan. Other residues of oxidative modification were not detected from the digested samples, possibly indicating the ion m/z=13,341 corresponding to NGF with nitrated Tyr52 and Trp99, to be the most abundant species. However this could also be due to an increased efficiency of ionization as compared to other peptides. Importantly, formation of 3,3'-dityrosine upon NGF oxidation was not observed by mass spectrometry, and the absence of this adduct was further confirmed by the lack of fluorescence at excitation/emission 320/410 nm.

Does Tyrosine Nitration Alter the Biological Activity of NGF?

Figure 8A:
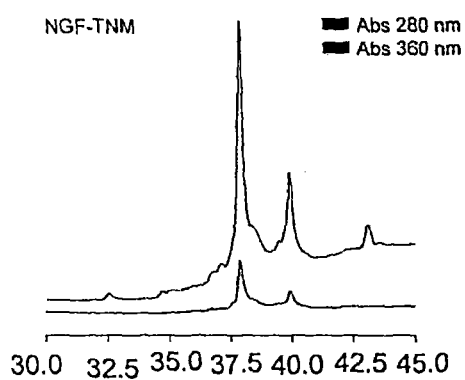
FIG. 8. Tetranitromethane treatment induced NGF nitration and oligomerization. (A) HPLC chromatogram of tetranitromethane (TNM)-treated NGF. NGF treated with 40-fold excess TNM eluted as two peaks at 37.9 and 39.9 minutes. Absorbance at 360 nm indicated the presence of nitrotyrosine in the eluted peaks. (B) Deconvoluted spectra of the eluent at 37.9 minutes showed a mass increase in NGF Chain A of 45 Da (to 13,297 Da) and 90 Da (to 13,342 Da) compared to that of native NGF (13,252 Da.
Figure 8B:
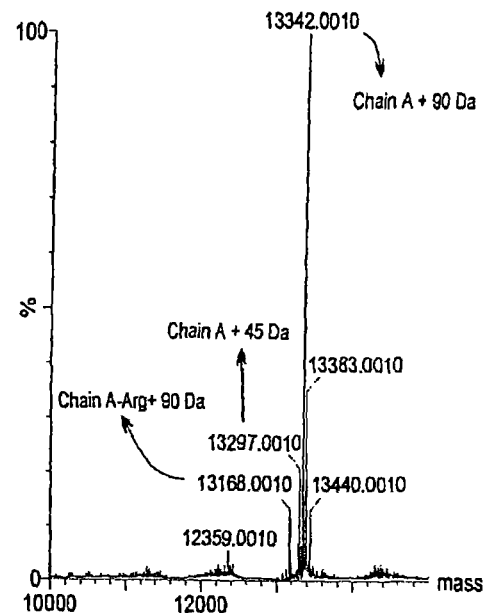
Figure 8C:
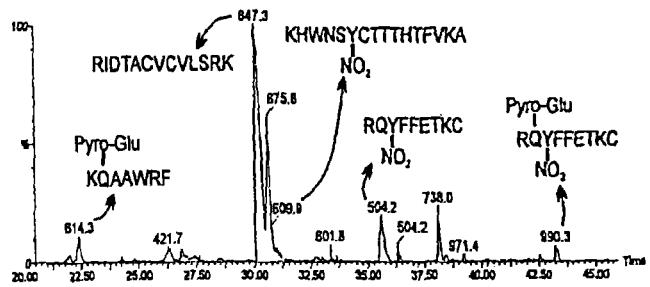
Figure 8D:
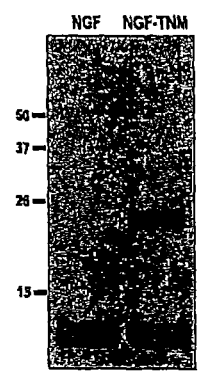

In order to ascertain whether tyrosine nitration was critical for modifying NGF biological activity, we treated NGF with tetranitromethane (TNM; 40-fold excess). TNM is commonly used to form 3-nitrotyrosine at alkaline pH in proteins. In the conditions used, TNM induced only tyrosine nitration as evidenced by mass spectrometry (see below). NGF treated with TNM separated into two products eluting at 37.9 and 39.9 minutes (FIG. 8A). As revealed by mass spectrometry, TNM treatment increased the molecular weight of NGF Chain A by 90 Da (from 13,252 to 13,342 Da; FIG. 8B), suggesting that the main product was a double nitrated species. However, the single nitrated species could also be observed at 13,297 Da (FIG. 8B). The same pattern was observed for Chain B of NGF. Tandem mass spectrometry of the digested products identified Tyr52 and Tyr79 as the nitrated residues (FIG. 8C), accounting for the total molecular weight change (FIG. 8B). Tryptophan nitration or 3,3'-dityrosine formation was not observed in TNM-treated NGF. The electrophoretic pattern of NGF treated with 40-fold excess of TNM was comparable to that observed in peroxynitrite-treated NGF, inducing the formation of NGF oligomers (FIG. 8D).

Figure 9A:
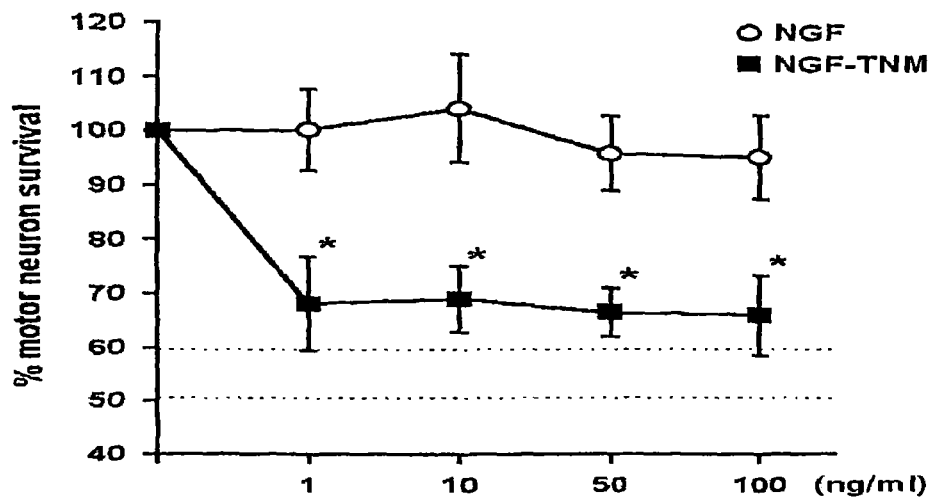
FIG. 9. Tetranitromethane-treated NGF induced $p75^{NTR}$-dependent motor neuron death. (A) Pure motor neuron cultures maintained with GDNF (1 ng/mL) were exposed to increasing concentrations of NGF previously treated with vehicle or 40-fold excess TNM (NGF-TNM). Dashed lines represent the SD of NONE (trophic factor deprivation). (B) Blocking antibodies to $p75^{NTR}$ (a-p75, 1:100, Chemicon #AB1554) prevented motor neuron death induced by NGF-TNM (100 ng/mL). Antibodies to $p75^{NTR}$ were added with NGF-TNM, 3 hours after motor neuron plating. Dashed lines represent the SD of GDNF. Motor neuron survival was determined 48 h after treatment. Data are expressed as percentage of GDNF, mean±SD. *Significantly different from GDNF (p≤0.05).
Figure 9B:
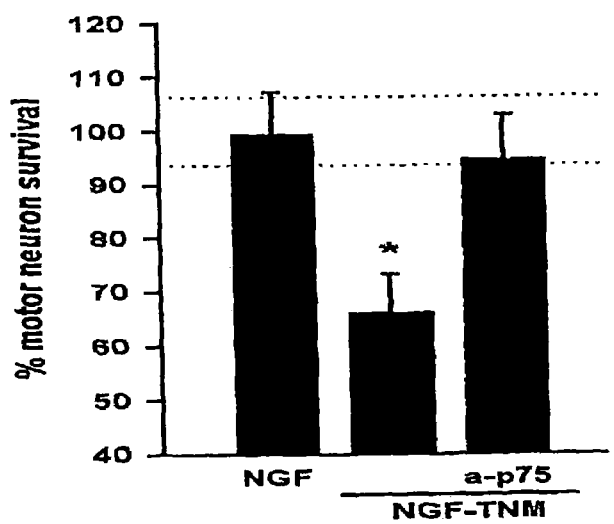

We then analyzed the effect of TNM-treated NGF on motor neuron survival. Similar to peroxynitrite-treated NGF, TNM-treated NGF induced 32% motor neuron loss in the absence of nitric oxide (FIG. 9A). Motor neuron death induced by TNM-treated NGF was also prevented by the addition of blocking antibodies to $p75^{NTR}$ (FIG. 9B), suggesting the triggering of the same apoptotic mechanism. Both nitration and NGF oligomerization were found as common modifications between TNM- and peroxynitrite-treated NGF.

Figure 10A:
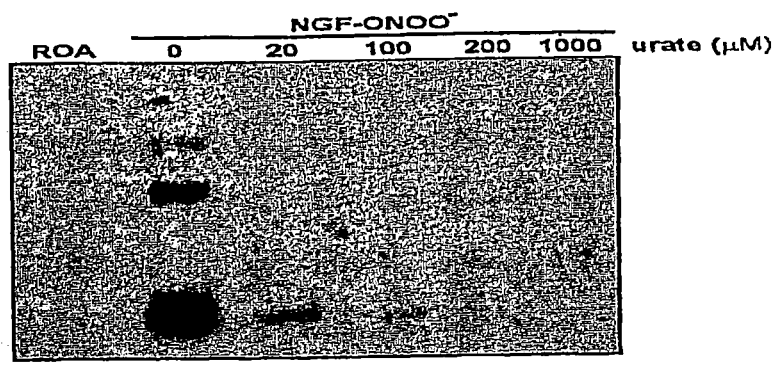
FIG. 10. Urate abolished the effect of peroxynitrite on NGF apoptotic activity. (A) Urate prevented in a dose dependent manner, tyrosine nitration and oligomerization of NGF. NGF was exposed to decomposed peroxynitrite (1 mM; ROA) or peroxynitrite (1 mM) in the presence of vehicle or increased concentrations of urate (20 to 1000 μM). Samples (100 ng) were analysed by SDS-15% polyacrylamide gel and Western Blot using a polyclonal antibody to nitrotyrosine. (B) NGF treated with peroxynitrite in the presence of urate did not affect neuronal survival. Motor neuron cultures were exposed to NGF (100 ng/mL) previously treated with peroxynitrite (1 mM) in the presence of vehicle (NGF-ONOO⁻) or urate (200 µM; NGF-ONOO⁻-urate). To eliminate the possibility of a direct effect of unreacted urate on motor neuron survival, the concentration of urate expected to be present in the culture media after addition of NGF-ONOO⁻-urate was added to the cultures exposed to NGF-ONOO⁻. Urate (100 nM) did not prevent motor neuron loss induced by NGF-ONOO⁻ (100 ng/mL). Motor neuron survival was determined 48 h after treatment. Dashed lines represent SD of GDNF. Data are expressed as percentage of GDNF, mean±SD. *Significantly different from GDNF ($p \leq 0.05$).
Figure 10B:
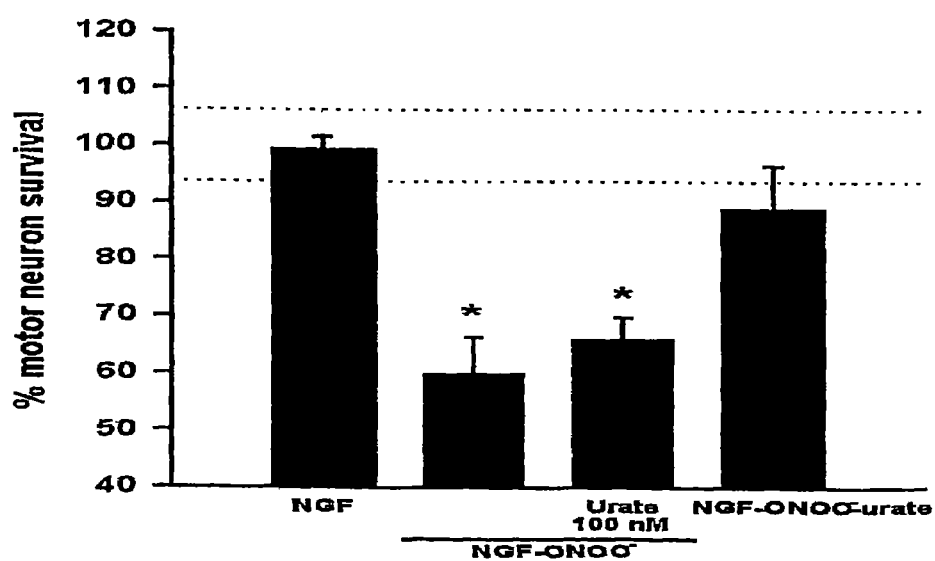

To further determine if nitration was conferring to NGF the capability of inducing motor neuron death, we treated NGF with peroxynitrite in the presence of urate. This compound, which is particularly effective at inhibiting nitration by peroxynitrite [49], prevented tyrosine nitration and oligomerization of NGF in a dose dependent manner (FIG. 10A). Moreover, urate (200 µM) abolished the apoptotic effect of peroxynitrite-treated NGF (FIG. 10B). As a control, 100 nM urate (the concentration expected to be present in the culture media after adding 100 ng/mL of NGF-ONOO− urate) did not prevent motor neuron loss induced by peroxynitrite-treated NGF (100 ng/mL) (FIG. 10B), implying that unreacted urate was not affecting motor neuron survival.

Secretion of Nitro-NGF by Stimulated Astrocytes.

The use of a specific antibody that binds to nitrated NGF, without cross-reacting with non-nitrated NGF, shows immunoreactive bands in the conditioned media from reactive astrocytes (see FIG. 13, which shows that monomeric and dimeric nitrated NGF species in the Western blot analysis of the conditioned media of FGF/LPS-stimulated astrocytes). This analysis shows that nitro-NGF is secreted under inflammatory conditions.

Neurite Outgrowth Promoting Activity.

FIG. 14 illustrates the fact that nitration of NGF increases the neurite outgrowth promoting activity of NGF.

Discussion

Because motor neuron death and astrocyte reactivity in ALS have been associated with the increased production of reactive oxygen and nitrogen species [28, 50, 51], we wished to investigate whether the oxidation or nitration of secreted NGF might enhance its apoptotic activity toward motor neurons.

Oxidation of NGF by peroxynitrite in vitro increased the potency for inducing apoptosis of motor neurons by 10,000-fold in the presence of nitric oxide. To the best of our knowledge, this is the first report of neurotrophin-elicited cell death in culture at physiologically relevant concentrations in the pg/mL range. Increased NGF levels have been implicated in the progressive death of motor neurons occurring in ALS [23-25]. We previously reported that spinal cord extracts from SOD1$^{G93A}$ ALS mice contain sufficient NGF to stimulate p75$^{NTR}$-dependent apoptosis of cultured motor neurons in the presence of an external source of nitric oxide [25]. However, the levels of NGF measured by ELISA in the degenerating spinal cord from SOD1$^{G93A}$ mice were in the range of picograms per mL [25], a concentration 10,000 times lower than necessary for purified NGF to induce apoptosis in pure motor neuron cultures and similar to the potency of peroxynitrite-treated NGF.

In a previous study, nitration of NGF by TNM did not modify NGF biological activity as assessed by induction of neurite outgrowth in sensory ganglia [52]. The difference in the expression of NGF receptors may account for the apparent contradictory results. Sensory ganglia express both TrkA and p75$^{NTR}$ [53, 54] while pure motor neuron cultures express p75$^{NTR}$ without detectable expression of TrkA [55]. Nitrated-NGF induced motor neuron apoptosis by a mechanism dependent on p75$^{NTR}$ signalling, as blocking antibodies to p75$^{NTR}$ or downregulation of p75$^{NTR}$ expression by antisense treatment completely prevented motor neuron death.

Figure 1:
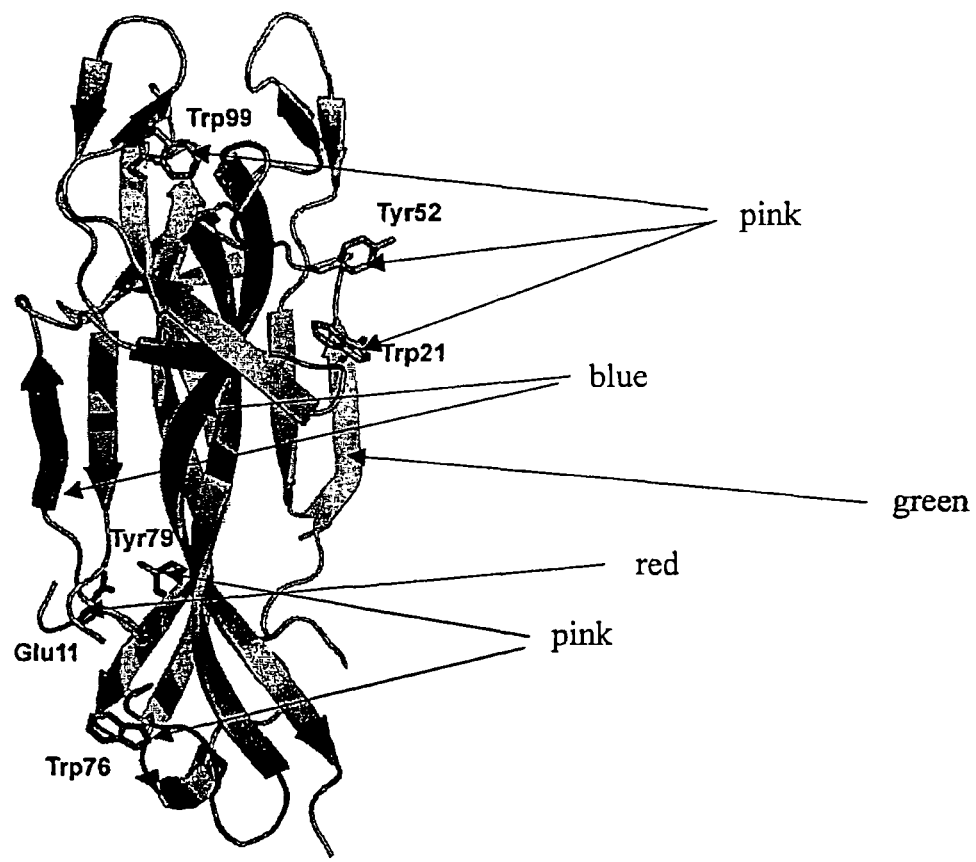
FIG. 1. Ribbon diagram of the NGF structure (PDB code 1BET). The two NGF monomers (green and blue) interact with each other through a largely hydrophobic interface [39]. The diagram shows the location of the two tyrosine and three tryptophan residues present in mouse NGF. The Tyr and Trp side chains from one monomer (green) are drawn in a stick representation and labeled (pink). Glu11 (red) from the opposite NGF monomer is also represented.

The gain of apoptotic activity by NGF was consistently associated with tyrosine nitration and abnormal oligomerization. Mouse NGF contains only two tyrosine residues at positions 52 and 79, both of which are accessible to the solvent [41]. The hydroxyl group of Tyr79 is involved in hydrogen bonding interactions to Glu11 from the opposing NGF monomer (FIG. 1). This interaction will reduce ionization of the tyrosine hydroxyl and thus render the residue less susceptible to radical-mediated oxidation, which may explain why Tyr79 was more resistant to nitration than Tyr52. The latter was readily nitrated by both peroxynitrite and TNM. Since Tyr52 is highly conserved and important for stabilizing NGF [43], its nitration may induce conformational changes in the protein that could facilitate aberrant protein interactions leading to oligomerization.

NGF oligomers ranged in size from dimers to octamers as evidenced by size exclusion chromatography coupled to real time-MALS. When purified high molecular weight oligomers were subjected to chromatography a second time, monomeric and dimeric peaks reappeared, indicating the formation of non-covalent oligomers. However, both peroxynitrite and TNM treatments led to the formation of higher oligomers that were stable in SDS-PAGE gels, implying a non-thiol dependent, covalent cross-linking of some subunits. Oligomerization of NGF was effectively prevented by urate. Urate is known to prevent peroxynitrite-induced tyrosine nitration by competing for carbonate and nitrogen dioxide radicals, suggesting radical formation is involved in the formation of oligomers. Although 3,3'-dityrosine cross-linking is one mechanism by which peroxynitrite can induce protein dimerization [56, 57], larger oligomers would require at least two different tyrosine residues to be crosslinked. If crosslinking only resulted from the generation of tyrosine radicals, nitration of Tyr52 would inhibit oligomerization. Furthermore, 3,3'-dityrosine could not be detected by fluorescence or by mass spectrometry. Therefore, oligomerization of NGF most likely involved other forms of cross-linking induced by peroxynitrite. In the presence of carbon dioxide, 30% of peroxynitrite forms carbonate radical plus nitrogen dioxide, which are both moderately strong oxidants that readily oxidize both tyrosine and tryptophan to form radicals [58]. Tyrosyl radicals also combine at near diffusion-limited rates with nitrogen dioxide to form 3-nitrotyrosine. Tryptophan oxidation yields multiple products, including N-formyl kynurenine and kynurenine, which can crosslink proteins [59]. On the other hand, tyrosyl radicals can also oxidize other amino acids, including tryptophan and cysteine by intramolecular electron transfer reactions [59, 60]. Within NGF, Tyr52 is spatially close to Trp21 (FIG. 1). Therefore, the oxidation of Tyr52 might transfer the radical to Trp21 and thereby facilitate covalent crosslinks between NGF molecules.

Peroxynitrite treated NGF potently stimulated p75-dependent apoptosis in motor neurons. Tyr52 and Trp21 in NGF are involved in the formation of the hydrophobic pocket that docks with the p75$^{NTR}$ cysteine-rich domain 2 (CRD2) [42]. Because Trp21 is a major part of the interface with p75$^{NTR}$, its oxidation products in vivo, might form covalent adducts to p75$^{NTR}$ and facilitate aberrant apoptotic signaling. However, other receptors could also be involved in the induction of apoptosis by peroxynitrite treated NGF. The precursor of NGF (proNGF) binds with lower affinity than NGF to p75$^{NTR}$, but it forms a high affinity-signalling complex by simultaneously binding to p75$^{NTR}$ and sortilin [61]. Also, p75$^{NTR}$ belongs to the TNFα receptor superfamily [62], and other members of this superfamily are known to require trimerization of their intracellular death domains for activation [63, 64]. Similarly, NGF oligomers could recruit additional p75 receptors and thereby promote trimerization of its death domain, and thus more strongly activate apoptotic signalling.

Because peroxynitrite treatment of NGF results in a gain-of-function, only a small fraction of nitrated protein is necessary to elicit apoptotic signalling. Peroxynitrite-treated NGF can be formed in pathological and inflammatory conditions where NGF up-regulation coincides with increased production of peroxynitrite and other nitrating species. The occurrence of oxidatively modified and nitrated NGF in vivo offers an exciting new mechanism by which neurotrophin signalling could be subverted under pathological conditions associated with increased oxidative stress.

List of Abbreviations:

ALS, amyotrophic lateral sclerosis; FGF, fibroblast growth factor; GDNF, glial derived neurotrophic factor; HPLC, high pressured liquid chromatography; MALS, multi-angle light scattering; NGF, nerve growth factor; NO, nitric oxide; NOS, nitric oxide sinthase; ONOO$^-$, peroxynitrite; p75$^{NTR}$, p75 neurotrophin receptor; ROA, reverse order addition; SOD1, superoxide dismutase 1; TNM, tetranitromethane.

Non-Limiting Embodiments

1. An inducer and/or stimulator of motor neuron apoptosis and/or of neurite outgrowth, which is:
   a modified neurotrophin in an isolated form, wherein at least one residue selected from Tyr and Trp residues comprises at least one nitro group; or
   a conservative fragment of said isolated form of modified neurotrophin, wherein said conservative fragment has retained at least one residue selected from Tyr and Trp residues, and wherein said conservative fragment has retained at least one nitro group on said at least one residue selected from Tyr and Trp residues, and has retained a capacity of inducing and/or stimulating motor neuron apoptosis and/or neurite outgrowth; or
   a conservative variant of said isolated form of modified neurotrophin or of said conservative fragment, wherein said conservative variant derives from said modified neurotrophin or from said conservative fragment by at least one amino acid substitution and/or deletion and/or addition, but has retained at least one residue selected from Tyr and Trp residues, and wherein said conservative variant has retained at least one nitro group on said at least one residue selected from Tyr and Trp residues, and has retained a capacity of inducing and/or stimulating motor neuron apoptosis and/or neurite outgrowth.

2. An inducer and/or stimulator of motor neuron apoptosis and/or neurite outgrowth, which is:
   a modified neurotrophin, wherein said modified neurotrophin is obtainable by post-translational nitrative modification of a native mature neurotrophin, by addition on said native mature neurotrophin of at least one nitro group on at least one residue selected from Tyr and Trp residues, and wherein said modified neurotrophin is in an isolated form; or
   a conservative fragment of said isolated form of modified neurotrophin, wherein said conservative fragment has retained at least one residue selected from Tyr and Trp residues, and wherein said conservative fragment has retained at least one nitro group on said at least one residue selected from Tyr and Trp residues, and has retained a capacity of inducing and/or stimulating motor neuron apoptosis and/or neurite outgrowth; or
   a conservative variant of said isolated form of modified neurotrophin or of said conservative fragment, wherein said conservative variant derives from said modified neurotrophin or from said conservative fragment by at least one amino acid substitution and/or deletion and/or addition, but has retained at least one residue selected from Tyr and Trp residues, and wherein said conservative variant has retained at least one nitro group on said at least one residue selected from Tyr and Trp residues, and has retained a capacity of inducing and/or stimulating motor neuron apoptosis and/or neurite outgrowth.

3. The inducer and/or stimulator of embodiment 1 or 2, wherein said modified neurotrophin is a modified neurotrophin monomer.

4. The inducer and/or stimulator of embodiment 1 or 2, wherein said modified neurotrophin is a modified neurotrophin oligomer.

5. The inducer and/or stimulator of embodiment 4, wherein said modified neurotrophin is a modified neurotrophin dimer.

6. The inducer and/or stimulator of embodiment 4, wherein said modified neurotrophin is a modified neurotrophin tetramer, or a modified neurotrophin hexamer, or a modified neurotrophin octamer.

7. An inducer and/or stimulator of motor neuron apoptosis and/or neurite outgrowth, which is a mixture of:
   at least two modified neurotrophin oligomers of any one of embodiments 4-6, wherein said at least two oligomers are of different oligomer species, and/or
   at least one modified neurotrophin monomer of embodiment 3, and at least one modified neurotrophin oligomer of any one of embodiments 4-6.

8. The inducer and/or stimulator of embodiment 7, which comprises at least one modified neurotrophin tetramer of any one of embodiments 4-6, and/or at least one modified neurotrophin hexamer of any one of embodiments 4-6, and/or at least one modified neurotrophin octamer of any one of embodiments 4-6.

9. The inducer and/or stimulator of any one embodiments 1-8, wherein said isolated form of modified neurotrophin does not comprise any non-nitrated pro-neurotrophin.

10. The inducer and/or stimulator of any one of the preceding embodiments, wherein said isolated form of modified neurotrophin does not comprise any non-nitrated mature neurotrophin.

11. The inducer and/or stimulator of any one of the preceding embodiments, which is in a pure form.

12. The inducer and/or stimulator of any one of the preceding embodiments, which is in a molecular configuration that does not impede its pro-apoptotic activity and/or its pro-neurite outgrowth activity.

13. The inducer and/or stimulator of any one of embodiments 1-12, wherein said neurotrophin is NGF, BDNF, NT-3 or NT-4.

14. The inducer and/or stimulator of any one of embodiment 13, wherein said neurotrophin is mature NGF.

15. The inducer and/or stimulator of any one of embodiment 13, wherein said neurotrophin is mature BDNF, mature NT-3 or mature NT-4.

16. The inducer and/or stimulator of any one of embodiments 1-15, wherein said at least one residue selected from Tyr and Trp residues that comprises at least one nitro group is a Tyr residue.

17. The inducer and/or stimulator of embodiment 16, wherein said Tyr residue is Tyr52 or Tyr79 of murine NGF, or Tyr52 or Tyr79 of human NGF.

18. The inducer and/or stimulator of any one of embodiments 1-15, wherein said at least one residue selected from Tyr and Trp residues that comprises at least one nitro group is a Trp residue.

19. The inducer and/or stimulator of embodiment 18, wherein said Trp residue is Trp99 or Trp21 or Trp76 of mouse NGF, or is Trp99 or Trp21 or Trp76 of human NGF.

20. The inducer and/or stimulator of any one of the preceding embodiments, wherein at least two of the Tyr and Trp residues of said neurotrophin bear a nitro group (at least one nitrogroup on each of said residues).

21. The inducer and/or stimulator of embodiment 20, wherein said at least two residues are two Tyr residues, or a Tyr residue and a Trp residue.

22. The inducer and/or stimulator of embodiment 20 or 21, wherein the number of Tyr and Trp residues of said neurotrophin that bear a nitro group (at least one nitrogroup on each of said residues) is of at least three, at least four, at least five, at least six, at least seven, at least eight, or at least nine.

23. The inducer and/or stimulator of any one of the preceding embodiments, wherein all the Tyr and Trp residues of said neurotrophin bear at least one nitrogroup.

24. The inducer and/or stimulator of any one of the preceding embodiments, wherein said modified neurotrophin is in a non-glycosylated form or in a glycosylated form.

25. A non-conservative fragment of an inducer and/or stimulator of any one of embodiments 1-24, or
   a non-conservative variant of an inducer and/or stimulator of any one of embodiments 1-24, which derives from said inducer and/or stimulator by at least one amino acid substitution and/or deletion and/or addition, wherein said non-conservative fragment or variant has lost the capacity of inducing and/or stimulating motor neuron apoptosis and/or neurite outgrowth.

26. The non-conservative fragment or variant of embodiment 25, for use as an antigen to induce an immune antibody response for the therapy and/or palliation and/or prevention of the apoptosis of motor neurons and/or the outgrowth of neurite.

27. The non-conservative fragment or variant of embodiment 25, for use as an agent for the treatment and/or palliation and/or prevention of pain and/or of a neurodegenerative disease or condition.

28. An antibody that binds to at least one inducer and/or stimulator according to any one of embodiments 1-24, without cross-reacting with the unmodified native neurotrophin, from which said inducer and/or stimulator derives.

29. The antibody of embodiment 28, which is a monoclonal antibody.

30. The antibody of embodiment 28 or 29, which is an antibody that binds to nitrated NGF.

31. The antibody of any one of embodiments 28-30, which is an scFv.

32. The antibody of any one embodiments 28-31, for use as an agent for passive immunization therapy and/or palliation and/or prevention of the apoptosis of motor neurons and/or the outgrowth of neurite.

33. The antibody of any one of embodiments 28-32, for use as an agent for the treatment and/or palliation and/or prevention of pain.

34. The antibody of any one of embodiments 28-32, for use as an agent for the treatment and/or palliation and/or prevention of a neurodegenerative disease or condition.

35. Ribosomal display system, which consists of at least one ribosome, to which at least one scFv of embodiment 31, as well as at least one mRNA encoding such a scFv, are attached.

36. Method of screening for compounds that are capable of inhibiting and/or blocking the apoptotic activity that a inducer and/or stimulator of any one of embodiments 1-24 may have on motor neurons, and/or the neurite outgrowth effect that a inducer and/or stimulator of any one of embodiments 1-24 may have on sensory ganglia, wherein candidate compounds are screened for their capacity of binding to at least one antibody of any one of embodiments 28-31, or to at least one ribosomal display system of embodiment 35, whereby such a binding capacity is indicative of a potential to inhibit and/or block said apoptotic activity and/or said neurite outgrowth effect.

37. A composition which comprises at least one non-conservative fragment or variant according to any one of embodiments 25-27, and/or at least one antibody according to any one of embodiments 28-34.

38. The non-conservative fragment or variant according to any one of embodiments 25-27, for use in the treatment and/or prevention and/or palliation of a neurodegenerative condition or disease, such as ALS (Amyotrophic Lateral Sclerosis), Alzheimer's disease, Huntington disease's, any disease or condition involving a memory deficit and/or a concentration disorder, as well as neuroinflammatory conditions or diseases.

39. The non-conservative fragment or variant according to any one of embodiments 25-27, for use in the treatment and/or prevention and/or palliation of a pain state or condition or feelings, and more particularly:
   neuropathic pain (more particularly, migraine, chronic migraine, probable analgesic-abuse headache PAAH, primary fibromyalgia syndrome PFMS, nerve-injury induced neuropathic pain, sciatic nerve lesions, chronic constriction injury),
   articular pain (more particularly, osteoarthritic conditions, osteoarthrosis, osteoarthritis),
   inflammatory pain,
   cancer pain.

40. The antibody according to any one of embodiments 28-34, for use in the treatment and/or prevention and/or palliation of a neurodegenerative condition or disease, such as ALS (Amyotrophic Lateral Sclerosis), Alzheimer's disease, Huntington disease's, any disease or condition involving a memory deficit and/or a concentration disorder, as well as neuroinflammatory conditions or diseases.

41. The antibody according to any one of embodiments 28-34, for use in the treatment and/or prevention and/or palliation of a pain state or condition or feelings, and more particularly:
   neuropathic pain (more particularly, migraine, chronic migraine, probable analgesic-abuse headache PAAH, primary fibromyalgia syndrome PFMS, nerve-injury induced neuropathic pain, sciatic nerve lesions, chronic constriction injury),
   articular pain (more particularly, osteoarthritic conditions, osteoarthrosis, osteoarthritis),
   inflammatory pain,
   cancer pain.

42. The composition of embodiment 37, for use in the treatment and/or prevention and/or palliation of a neurodegenerative condition or disease, such as ALS (Amyotrophic Lateral Sclerosis), Alzheimer's disease, Huntington disease's, Multiple Sclerosis, any disease or condition involving a memory deficit and/or a concentration disorder, as well as neuroinflammatory conditions or diseases.

43. The composition of embodiment 37, for use in the treatment and/or prevention and/or palliation of a pain state or condition or feelings, and more particularly:
   neuropathic pain (more particularly, migraine, chronic migraine, probable analgesic-abuse headache PAAH, primary fibromyalgia syndrome PFMS, nerve-injury induced neuropathic pain, sciatic nerve lesions, chronic constriction injury),
   articular pain (more particularly, osteoarthritic conditions, osteoarthrosis, osteoarthritis),
   inflammatory pain,
   cancer pain.

44. The inducer and/or stimulator of any one of embodiments 1-24, for use as an agent useful for the induction and/or the stimulation of motor neuron apoptosis and/or for the induction and/or the stimulation of neurite outgrowth.

45. The inducer and/or stimulator of any one of embodiments 1-24, for use in the treatment and/or prevention and/or palliation of a disease, condition or trauma selected from the group comprising neuropathy, nerve injury, stroke, spinal cord injury, and neurodegenerative illness.

46. A composition, which comprises at least one inducer and/or stimulator according to any one of embodiments 1-24.

47. The composition of embodiment 46, for use in the treatment and/or prevention and/or palliation of a disease, condition or trauma selected from the group comprising neuropathy, nerve injury, stroke, spinal cord injury, and neurodegenerative illness.

48. An in vitro method for the diagnosis of a neurodegenerative condition or disease, and/or of a pain state or condition or feeling, which comprises:
   contacting a biological sample at one antibody according to any one of embodiments 28-34,
   determining whether said at least one antibody binds to a ligand contained in said biological sample,
   whereby such a binding is indicative or predictive of said disease, state, condition or feeling.

BIBLIOGRAPHIC REFERENCES

[1] Snider, W. D. Functions of the neurotrophins during nervous system development: what the knockouts are teaching us. *Cell* 77: 627-638; 1994.

[2] Chao, M. V. Neurotrophins and their receptors: a convergence point form many signalling pathways. *Nat. Rev. Neurosci.* 4: 299-309; 2003.

[3] Barker, P. A. p75 NTR is positively promiscuous: novel partners and new insights. *Neuron* 42: 529-533; 2004.

[4] Nykjaer, A.; Willnow, T. E.; Petersen, C. M. p75NTR—live or let die. *Curr. Opin. Neurobiol.* 15: 49-57; 2005.

[5] Levi-Montalcini, R.; Skaper, S. D.; Dal Toso, R.; Petrelli, L.; Leon, A. Nerve growth factor: from neurotrophin to neurokine. *Trends Neurosci.* 19: 514-520; 1996.

[6] Fahnestock, M.; Scott, S. A.; Jetté, N.; Weingartner, J. A.; Crutcher, K. A. Nerve growth factor mRNA and protein levels measured in the same tissue from normal and Alzheimer's disease parietal cortex. *Mol. Brain. Res.* 4: 175-178; 1996.

[7] Widenfalk, J.; Lundstromer, K.; Jubran, M.; Brene, S.; Olson, L. Neurotrophic factors and receptors in the immature and adult spinal cord after mechanical injury or kainic acid. *J. Neurosci.* 21: 3457-3475; 2001.

[8] Beattie, M. S.; Harrington, A. W.; Lee, R.; Kim, J. Y.; Boyce, S. L.; Longo, F. M.; Bresnahan, J. C.; Hempstead, B. L.; Yoon, S. O. ProNGF induces p75-mediated death of oligodendrocytes following spinal cord injury. *Neuron* 36: 375-386; 2002.

[9] Majdan, M.; Miller, F. Neuronal life and death decisions: functional antagonism between the Trk and p75 neurotrophin receptors. *Int. J. Devi. Neurosci.* 17: 153-161; 1999.

[10] Lee, F. S.; Kim, A. H.; Khursigara, G.; Chao, M. V. The uniqueness of being a neurotrophin receptor. *Curr. Opin. Neurobiol.* 11: 281-286; 2001.

[11] Barrett, G. L. The p75 neurotrophin receptor and neuronal apoptosis. *Prog. Neurobiol.* 61: 205-229; 2000.

[12] Dechant, G.; Barde, Y-A. The neurotrophin receptor p75$^{NTR}$: novel functions and implications for diseases of the nervous system. *Nature Neurosci.* 5: 1131-1136; 2002.

[13] Yan, Q.; Johnson, E. M. Jr. An immunohistochemical study of the nerve growth factor receptor in developing rats. *J. Neurosci.* 8: 3481-3498; 1988.

[14] Ferri, C. C.; Moore, F. A.; Bisby, M. A. Effects of facial nerve injury on mouse motoneurons lacking the p75 low-affinity neurotrophin receptor. *J. Neurobiol.* 34: 1-9; 1998.

[15] Koliatsos, V. E.; Crawford, T. O.; Price, D. L. Axotomy induces nerve growth factor receptor immunoreactivity in spinal motor neurons. *Brain Res.* 549: 297-304; 1991.

[16] Rende, M.; Giambanco, I.; Buratta, M.; Tonali, P. Axotomy induces a different modulation of both low-affinity nerve growth factor receptor and choline acetyltransferase between adult rat spinal and brainstem motoneurons. *J. Comp. Neurol.* 363: 249-263; 1995.

[17] Seeburger, J. L; Tarras, S.; Natter, H.; Springer, J. E. Spinal cord motoneurons express p75NGFR and p145trkB mRNA in amyotrophic lateral sclerosis. *Brain Res.* 621: 111-115; 1993.

[18] Lowry, K. S.; Murray, S. S.; McLean, C. A.; Talman, P.; Mathers, S.; Lopes, E. C.; Cheema, S. S. A potential role for the p75 low-affinity neurotrophin receptor in spinal motor neuron degeneration in murine and human amyotrophic lateral sclerosis. *Amyotroph. Lateral Scler. Other Motor Neuron Disord.* 2: 127-134; 2001.

[19] Wiese, S.; Metzger, F.; Holtmann, B.; Sendtner, M. The role of p75NTR in modulating neurotrophin survival effects in developing motoneurons. *Eur. J. Neurosci.* 11: 1668-1676; 1999.

[20] Lowry, K. S.; Murray, S. S.; Coulson, E. J.; Epa, R.; Bartlett, P. F.; Barrett, G.; Cheema, S. S. Systemic administration of antisense p75(NTR) oligodeoxynucleotides rescues axotomised spinal motor neurons. *J. Neurosci. Res.* 64: 11-17; 2001.

[21] Kust, B. M.; Brouwer, N.; Mantingh, I. J.; Boddeke, H. W.; Copray, J. C. Reduced p75NTR expression delays disease onset only in female mice of a transgenic model of familial amyotrophic lateral sclerosis. *Amyotroph. Lateral Scler. Other Motor Neuron Disord.* 4: 100-105; 2003.

[22] Copray, J. C.; Jaarsma, D.; Kust, B. M.; Bruggeman, R. W.; Mantingh, I.; Brouwer, N.; Boddeke, H. W. Expression of the low affinity neurotrophin receptor p75 in spinal motoneurons in a transgenic mouse model for amyotrophic lateral sclerosis. *Neuroscience* 116: 685-694; 2003.

[23] Turner, B. J.; Cheah, I. K.; Macfarlane, K. J.; Lopes, E. C.; Petratos, S.; Langford, S. J.; Cheema, S. S. Antisense peptide nucleic acid-mediated knockdown of the p75 neurotrophin receptor delays motor neuron disease in mutant SOD1 transgenic mice. *J. Neurochem.* 87: 752-763; 2003.

[24] Turner, B. J.; Rembach, A.; Spark, R.; Lopes, E. C.; Cheema, S. S. Opposing effects of low and high-dose clozapine on survival of transgenic amyotrophic lateral sclerosis mice. *J. Neurosci. Res.* 74: 605-613; 2003.

[25] Pehar, M.; Cassina, P.; Vargas, M. R.; Castellanos, R.; Viera, L.; Beckman, J. S.; Estevez, A. G.; Barbeito, L. Astrocytic production of nerve growth factor in motor neuron apoptosis: implications for amyotrophic lateral sclerosis. *J. Neurochem.* 89: 464-473; 2004.

[26] Radi, R. Peroxynitrite reactions and diffusion in biology. *Chem. Res. Toxicol.* 11: 720-721; 1998.

[27] Beckman, J. S.; Koppenol, W. H. Nitric oxide, superoxide, and peroxynitrite: the good, the bad, and ugly. *Am. J. Physiol.* 271: 01424-1437; 1996.

[28] Beckman, J. S.; Estévez, A. G.; Crow, J. P.; Barbeito, L. Superoxide dismutase and the death of motoneurons in ALS. *Trends Neurosci.* 11: S15-S20; 2001.

[29] Radi, R.; Peluffo, G.; Alvarez, M. N.; Naviliat, M.; Cayota, A. Unraveling peroxynitrite formation in biological systems. *Free Radic. Biol. Med.* 30: 463-488; 2001.

[30] Radi, R. Nitric oxide, oxidants, and protein tyrosine nitration. *Proc. Natl. Acad. Sci. U.S.A.* 101: 4003-4008; 2004.

[31] Ischiropoulos, H. Biological selectivity and functional aspects of protein tyrosine nitration. *Biochem. Biophys. Res. Commun.* 305: 776-783; 2003.

[32] Haddad, I. Y.; Crow, J. P.; Hu, P.; Ye, Y.; Beckman, J. Matalon, S. Concurrent generation of nitric oxide and superoxide damages surfactant protein A. *Am. J. Physiol.* 267: L242-249; 1994.

[33] Crow, J. P.; Ye, Y. Z.; Strong, M.; Kirk, M.; Barnes, S.; Beckman, J. S. Superoxide dismutase catalyzes nitration of tyrosines by peroxynitrite in the rod and head domains of neurofilament-L. *J. Neurochem.* 69: 1945-1953; 1997.

[34] Cassina, A. M; Hodara, R.; Souza, J. M.; Thomson, L.; Castro, L.; Ischiropoulos, H.; Freeman, B. A.; Radi, R. Cytochrome c nitration by peroxynitrite. *J. Biol. Chem.* 275: 21409-21415; 2000.

[35] Vadseth, C.; Souza, J. M.; Thomson, L.; Seagraves, A.; Nagaswami, C.; Scheiner, T.; Torbet, J.; Vilaire, G.; Bennett, J. S.; Murciano, J. C.; Muzykantov, V.; Penn, M. S.; Hazen, S. L.; Weisel, J. W.; Ischiropoulos, H. Pro-thrombotic state induced by post-translational modification of fibrinogen by reactive nitrogen species. *J. Biol. Chem.* 279: 8820-8826; 2004.

[36] Balafanova, Z.; Bolli, R.; Zhang, J.; Zheng, Y.; Pass, J. M.; Bhatnagar, A.; Tang, X.-L.; Wang, O.; Cardwell, E.; Ping, P. *J. Biol. Chem.* 277: 15021-15027; 2002.

[37] Ji, Y.; Neverova, I.; Van Eyk, J. E.; Bennett, B. M. Nitration of tyrosine 92 mediates the activation of rat microsomal glutathione s-transferase by peroxynitrite. *J. Biol. Chem.* 281: 1986-1991; 2006.

[38] Bradshaw, R. A. Nerve growth factor. *Annu. Rev. Biochem.* 47: 191-216; 1978.

[39] McDonald, N. Q.; Lapatto, R.; Murray-Rust, J.; Gunning, J.; Wlodawer, A.; Blundell, T. L. New protein fold revealed by a 2.3-A resolution crystal structure of nerve growth factor. *Nature* 354: 411-414; 1991.

[40] Moore, J. B. Jr; Mobley, W. C.; Shooter, E. M. Proteolytic modification of the beta nerve growth factor protein. *Biochemistry* 13: 833-840; 1974.

[41] Bradshaw, R. A.; Murray-Rust, J.; Ibanez, C. F.; McDonald, N. Q.; Lapatto, R.; Blundell, T. L. Nerve growth factor: structure/function relationships. *Protein Sci.* 3: 1901-1913; 1994.

[42] He, X. L.; Garcia, K. C. Structure of nerve growth factor complexed with the shared neurotrophin receptor p75. *Science* 304: 870-875; 2004.

[43] Ibanez, C. F.; Hallbook, F.; Ebendal, T.; Persson, H. Structure-function studies of nerve growth factor: functional importance of highly conserved amino acid residues. *EMBO J.* 9: 1477-1483; 1990.

[44] Henderson, C. E.; Bloch-Gallego, E.; Camu, W. Purification and culture of embryonic motor neurons. In: Cohen, J.; Wilkin, G., eds. *Neural cell culture: a practical approach*. Oxford: IRL Press; 1995: 69-81.

[45] Florez-McClure, M. L.; Linseman, D. A.; Chu, C. T.; Barker, P. A.; Bouchard, R. J.; Le, S. S.; Laessig, T. A.; Heidenreich, K. A. The p75 neurotrophin receptor can induce autophagy and death of cerebellar Purkinje neurons. *J. Neurosci.* 24: 4498-4509; 2004.

[46] Estévez, A. G.; Spear, N.; Manuel, S. M.; Radi, R.; Henderson, C. E.; Barbeito, L.; Beckman, J. S, Nitric oxide and superoxide contribute to motor neuron apoptosis induced by trophic factor deprivation. *J. Neurosci.* 18: 923-931; 1998.

[47] Estévez, A. G.; Crow, J. P.; Sampson, J. B.; Reiter, C.; Zhuang, Y.; Richardson, G. J.; Tarpey, M. M.; Barbeito, L.; Beckman, J. S. Induction of nitric oxide dependent apoptosis in motor neurons by zinc-deficient superoxide dismutase. *Science* 286: 2498-2500; 1999.

[48] Raoul, C.; Estevez, A. G.; Nishimune, H.; Cleveland, D. W.; deLapeyrière, O.; Henderson, C. E.; Haase, G.; Pettmann, B. Motoneuron death triggered by a specific pathway downstream of Fas: potentiation by ALS-linked SOD1 mutations. *Neuron* 35: 1067-1083; 2002.

[49] Hooper, D. C.; Spitsin, S.; Kean, R. B.; Champion, J. M.; Dickson, G. M.; Chaudhry, I.; Koprowski, H. Uric acid, a natural scavenger of peroxynitrite, in experimental allergic encephalomyelitis and multiple sclerosis. *Proc. Natl. Acad. Sci. U.S.A.* 95: 675-680; 1998.

[50] Beal, M. F. Oxidatively modified proteins in aging and disease. *Free Radic. Biol. Med.* 32: 797-803; 2002.

[51] Ischiropoulos, H.; Beckman, J. S. Oxidative stress and nitration in neurodegeneration: cause, effect, or association? *J. Clin. Invest.* 111: 163-169; 2003.

[52] Frazier, W. A.; Hogue-Angeletti, R. A.; Sherman, R.; Bradshaw, R. A. Topography of mouse 2.5S nerve growth factor. Reactivity of tyrosine and tryptophan. *Biochemistry* 12: 3281-3293; 1973.

[53] Windebank, A. J.; Blexrud, M. D. Characteristics of neurite outgrowth from rat spinal ganglia: effects of serum and segmental level. *J. Neuropathol. Exp. Neurol.* 45: 683-691; 1986.

[54] Williams, R.; Backstrom, A.; Kullander, K.; Hallbook, F.; Ebendal, T. Developmentally regulated expression of mRNA for neurotrophin high-affinity (trk) receptors within chick trigeminal sensory neurons. *Eur. J. Neurosci.* 7: 116-128; 1995.

[55] Xu, H.; Federoff, H.; Maragos, J.; Parada, L. F.; Kessler, J. A. Viral transduction of trkA into cultured nodose and spinal motor neurons conveys NGF responsiveness. *Dev. Biol.* 163: 152-161; 1994.

[56] Souza, J. M.; Giasson, B. I.; Chen, Q.; Lee, V. M.; Ischiropoulos, H. Dityrosine cross-linking promotes formation of stable alpha-synuclein polymers. Implication of nitrative and oxidative stress in the pathogenesis of neurodegenerative synucleinopathies. *J. Biol. Chem.* 275: 18344-18349; 2000.

[57] Reynolds, M. R.; Berry, R. W.; Binder, L. I. Site-specific nitration and oxidative dityrosine bridging of the tau protein by peroxynitrite: implications for Alzheimer's disease. *Biochemistry* 44: 1690-1700; 2005.

[58] Radi, R.; Denicola, A.; Freeman, B. A. Peroxynitrite reactions with carbon dioxide-bicarbonate. *Methods Enzymol.* 301: 353-367; 1999.

[59] Zhang, H.; Andrekopoulos, C.; Joseph, J.; Crow, J.; Kalyanaraman, B. The carbonate radical anion-induced covalent aggregation of human copper, zinc superoxide dismutase, and alpha-synuclein: intermediacy of tryptophan- and tyrosine-derived oxidation products. *Free Radic. Biol. Med.* 36: 1355-1365; 2004.

[60] Zhang, H.; Xu, Y.; Joseph, J.; Kalyanaraman, B. Intramolecular electron transfer between tyrosyl radical and cysteine residue inhibits tyrosine nitration and induces thiyl radical formation in model peptides treated with myeloperoxidase, H2O2, and NO2-: EPR SPIN trapping studies. *J. Biol. Chem.* 280: 40684-40698; 2005.

[61] Nykjaer, A.; Lee, R.; Teng, K. K.; Jansen, P.; Madsen, P.; Nielsen, M. S.; Jacobsen, C.; Kliemannel, M.; Schwarz, E.; Willnow, T. E.; Hempstead, B. L.; Petersen, C. M. Sortilin is essential for proNGF-induced neuronal cell death. *Nature* 427: 843-848; 2004.

[62] Meakin, S. O.; Shooter, E. M. The nerve growth factor family of receptors. *Trends Neurosci.* 15: 323-331; 1992.

[63] Park, Y. C.; Burkitt, V.; Villa, A. R.; Tong, L.; Wu, H. Structural basis for self-association and receptor recognition of human TRAF2. *Nature* 398: 533-538.

[64] Berglund, H.; Olerenshaw, D.; Sankar, A.; Federwisch, M.; McDonald, N. Q.; Driscoll, P. C. The three-dimensional solution structure and dynamic properties of the human FADD death domain. *J. Mol. Biol.* 302: 171-188; 2000.

---

The invention claimed is:

1. An isolated hNGF-binding monoclonal antibody that binds specifically to hNGF (SEQ ID NO:2) when it has been nitrated on Trp21, Tyr52, Trp76, Tyr79, or Trp99, but does not bind to hNGF (SEQ ID NO:2) when it has not been nitrated.

2. The isolated antibody of claim 1, wherein the antibody reacts specifically with monomeric and dimeric nitrated NGF species in a Western blot analysis of the conditioned media of FGF/LPS-stimulated astrocytes.

3. The isolated antibody of claim 1, wherein the antibody is a chimeric antibody.

4. The isolated antibody of claim 1, wherein the antibody is a humanized antibody.

5. The isolated antibody of claim 1, wherein the antibody is a human antibody.

6. The isolated antibody of claim 1, wherein the antibody binds to the epitope QYFFETK (SEQ ID NO:7) that has been nitrated on its tyrosine (Y) residue.

7. A composition comprising the isolated antibody of claim 1 and a pharmaceutically acceptable carrier.

8. The isolated antibody of claim 1, wherein the antibody binds specifically to hNGF (SEQ ID NO:2) when it has been nitrated on Trp21.

9. The isolated antibody of claim 1, wherein the antibody binds specifically to hNGF (SEQ ID NO:2) when it has been nitrated on Tyr52.

10. The isolated antibody of claim 1, wherein the antibody binds specifically to hNGF (SEQ ID NO:2) when it has been nitrated on Trp76.

11. The isolated antibody of claim 1, wherein the antibody binds specifically to hNGF (SEQ ID NO:2) when it has been nitrated on Tyr79.

12. The isolated antibody of claim 1, wherein the antibody binds specifically to hNGF (SEQ ID NO:2) when it has been nitrated on Trp99.

* * * * *